US009421241B2

(12) United States Patent
Sullivan et al.

(10) Patent No.: US 9,421,241 B2
(45) Date of Patent: Aug. 23, 2016

(54) THERAPEUTIC MODULATION OF OCULAR SURFACE LUBRICATION

(71) Applicants: The Regents of the University of California, Oakland, CA (US); Schepens Eye Research Institute, Boston, MA (US)

(72) Inventors: Benjamin Sullivan, San Diego, CA (US); Tannin A. Schmidt, Calgary (CA); David A. Sullivan, Boston, MA (US)

(73) Assignees: THE REGENTS OF THE UNIVERSITY OF CALIFORNIA, Oakland, CA (US); SCHEPENS EYE RESEARCH INSTITUTE, Boston, MA (US)

( * ) Notice: Subject to any disclaimer, the term of this patent is extended or adjusted under 35 U.S.C. 154(b) by 0 days.

(21) Appl. No.: 14/831,317

(22) Filed: Aug. 20, 2015

(65) Prior Publication Data

US 2016/0015780 A1    Jan. 21, 2016

Related U.S. Application Data

(60) Division of application No. 12/940,425, filed on Nov. 5, 2010, now Pat. No. 9,138,457, which is a continuation of application No. PCT/US2009/043015, filed on May 6, 2009.

(60) Provisional application No. 61/051,112, filed on May 7, 2008.

(51) Int. Cl.

| | |
|---|---|
| A61K 31/568 | (2006.01) |
| A61K 31/728 | (2006.01) |
| A61K 38/14 | (2006.01) |
| A61K 9/00 | (2006.01) |
| A61K 31/715 | (2006.01) |
| A61K 38/13 | (2006.01) |
| A61K 38/18 | (2006.01) |
| A61K 38/17 | (2006.01) |
| A61K 45/06 | (2006.01) |
| A61K 31/685 | (2006.01) |
| A61K 31/688 | (2006.01) |

(52) U.S. Cl.
CPC ............. *A61K 38/14* (2013.01); *A61K 9/0048* (2013.01); *A61K 9/0051* (2013.01); *A61K 31/568* (2013.01); *A61K 31/685* (2013.01); *A61K 31/688* (2013.01); *A61K 31/715* (2013.01); *A61K 31/728* (2013.01); *A61K 38/13* (2013.01); *A61K 38/17* (2013.01); *A61K 38/1709* (2013.01); *A61K 38/1841* (2013.01); *A61K 45/06* (2013.01)

(58) Field of Classification Search
CPC ........................... A61K 31/568; A61K 31/728
See application file for complete search history.

(56) References Cited

U.S. PATENT DOCUMENTS

| | | | |
|---|---|---|---|
| 4,801,619 A | 1/1989 | Lindblad | |
| 4,964,206 A | 10/1990 | Knoll et al. | |
| 5,286,829 A | 2/1994 | Fedorov et al. | |
| 5,351,100 A | 9/1994 | Schwenzfeier et al. | |
| 5,702,456 A | 12/1997 | Pienkowski | |
| 5,942,558 A | 8/1999 | Korb | |
| 6,107,289 A | 8/2000 | Sullivan | |
| 6,635,267 B1 | 10/2003 | Miyoshi et al. | |
| 6,689,748 B1 | 2/2004 | Theoharides | |
| 6,815,074 B2 | 11/2004 | Aguado et al. | |
| 6,940,580 B2 | 9/2005 | Winterton et al. | |
| 7,014,860 B1 | 3/2006 | Kawata et al. | |
| 7,329,415 B2 | 2/2008 | Lally et al. | |
| 7,361,738 B2 | 4/2008 | Turner et al. | |
| 7,811,267 B2 | 10/2010 | Norrby et al. | |
| 2003/0008154 A1 | 1/2003 | Aguado et al. | |
| 2003/0130324 A1 | 7/2003 | McAvoy et al. | |
| 2003/0134132 A1 | 7/2003 | Winterton et al. | |
| 2003/0219909 A1 | 11/2003 | Lally et al. | |
| 2004/0009893 A1 | 1/2004 | Wang et al. | |
| 2004/0029913 A1 | 2/2004 | Dalton et al. | |
| 2004/0157073 A1 | 8/2004 | Burrell et al. | |
| 2005/0063996 A1 | 3/2005 | Peyman | |
| 2005/0129778 A1 | 6/2005 | Mulye | |

(Continued)

FOREIGN PATENT DOCUMENTS

| | | |
|---|---|---|
| WO | 9406485 | 3/1994 |
| WO | 0027421 | 5/2000 |

(Continued)

OTHER PUBLICATIONS

Zappone et al., 2007, "Adsorption, Lubricatin, and Wear of Lubricin on Model Surfaces: Polymer Brush-Like Behavior of a Glycoprotein," Biophysical Journal, 92:1693-1708.

(Continued)

*Primary Examiner* — Zohreh Fay

(74) *Attorney, Agent, or Firm* — Sutherland Asbill & Brennan LLP

(57) ABSTRACT

Provided herein are ophthalmically acceptable pharmaceutical compositions comprising PRG4 or lubricant fragments and a PRG4 inducing compound. The PRG4 inducing compound in the pharmaceutical composition of the present invention upregulates PRG4 expression and localization in the ocular surface for efficient surface boundary lubrication. In some instances, pharmaceutical compositions described herein are utilized for treating ophthalmic conditions, e.g., ocular boundary deficiency and symptoms associated therewith.

20 Claims, 6 Drawing Sheets

(56) References Cited

U.S. PATENT DOCUMENTS

| | | |
|---|---|---|
| 2005/0153056 A1 | 7/2005 | Winterton et al. |
| 2005/0196370 A1 | 9/2005 | Yu et al. |
| 2005/0287223 A1 | 12/2005 | Peyman |
| 2006/0067927 A1 | 3/2006 | Chandrasekaran et al. |
| 2006/0228394 A1 | 10/2006 | Peyman |
| 2006/0281739 A1 | 12/2006 | Gadek et al. |
| 2007/0031471 A1 | 2/2007 | Peyman |
| 2007/0191268 A1 | 8/2007 | Flannery et al. |
| 2007/0249557 A1 | 10/2007 | Jay |
| 2007/0264226 A1 | 11/2007 | Karagoezian et al. |
| 2007/0275032 A1 | 11/2007 | Wimmer et al. |
| 2007/0292496 A1 | 12/2007 | Vanrell et al. |
| 2008/0053845 A1 | 3/2008 | Newman |
| 2008/0076829 A1 | 3/2008 | Dalton et al. |
| 2008/0094573 A1 | 4/2008 | Vermette et al. |
| 2008/0097606 A1 | 4/2008 | Cragg et al. |
| 2008/0197324 A1 | 8/2008 | Zhao et al. |
| 2008/0213274 A1 | 9/2008 | Sabbadini et al. |
| 2009/0060933 A1 | 3/2009 | Estell et al. |
| 2009/0068247 A1 | 3/2009 | Jay |
| 2009/0160074 A1 | 6/2009 | Pruitt et al. |
| 2010/0092452 A1 | 4/2010 | Sullivan et al. |
| 2011/0059902 A1 | 3/2011 | Sullivan et al. |
| 2011/0070222 A1 | 3/2011 | Sullivan et al. |
| 2011/0142908 A1 | 6/2011 | Sullivan et al. |
| 2012/0321611 A1 | 12/2012 | Sullivan et al. |

FOREIGN PATENT DOCUMENTS

| | | |
|---|---|---|
| WO | 03030941 | 4/2003 |
| WO | 03057270 | 7/2003 |
| WO | 2004035736 | 4/2004 |
| WO | 2005016130 | 2/2005 |
| WO | 2005027933 | 3/2005 |
| WO | 2005110473 | 11/2005 |
| WO | 2006094026 | 9/2006 |

OTHER PUBLICATIONS

Jay et al., 2010, "Prevention of Cartilage Degeneration and Restoration of Chondroprotection by Lubricin Tribosupplementation in the Rat Following Anterior Cruciate Ligament Transection," Arthritis & Rheumatism, 62(8):2382-2391.

Written Opinion for PCT/US09/43015 dated Jun. 7, 2009 (6 pages).

Japanese Office Action dated Nov. 20, 2012 for Japanese Application No. 2011-508534.

Japanese Office Action dated Nov. 20, 2012 for Japanese Application No. 2011-508633.

Japanese Office Action dated Nov. 20, 2012 for Japanese Application No. 2011-508634.

Foulks et al., 2008, "Pharmacological Management of Dry Eye in the Elderly Patient," Drugs & Aging, 25(2):105-118.

Supplementary European Search Report for EP Application No. 09 74 3588 dated Jul. 11, 2011.

International PCT Search Report for PCT/US2009/043015 dated Jun. 16, 2009.

International Search Report for PCT/US2010/53797 dated Jan. 6, 2011 (2 pages).

Disclosure under 37 C.F.R. 1.56 (2 pages).

Ikegawa et al., "Isolation, Characterization and Mapping of the Mouse and Human PRG4 (proteoglycan 4) Genes," Cytogenet Cell Genes, 2000, 90:291-297.

Jay et al., "Characterization of a Bovine Synovial Fluid Lubricating Factor. II. Comparison with Purified Ocular and Salivary Mucin," Connective Tissue Research, 1992, 28:89-98.

Sullivan et al., "Proteoglycan 4mRNA Expression in Human Corneal and Conjunctional Epithelial Cells," May 10, 2007, Poster at the Annual Meeting of the Association for Research in Vision and Ophthamology.

Sullivan et al., "Proteoglycan 4mRNA Expression in Human Corneal and Conjunctional Epithelial Cells," Invest. Ophthamol. Vis. Sci., Feb. 2007, 48:E-Abstract 795.

Jones et al., "Elastohydrodynamics of the Eyelid Wiper," Bull Math Biol., 2008, 70(2):323-43.

Tsai et al., 2006, "Proteomic Analysis of Human Meibomian Gland Secretions," Br. J. Ophthalmol, 90:372-377.

DuRaine et al., "Regulation of the Friction Coefficient of Articular Cartilage by TGF-Beta1 and IL-1Beta," Journal of Orthopaedic Research, 2008, 249-256.

Schmidt et al., "Transcription, Translation, and Function of Lubricin, a Boundary Lubricant, at the Ocular Surface," JAMA Ophthalmol., 2003, 131(6):1-23.

Gleghorn et al., "Role of Electrostatic Interaction in the Lubrication of Articular Cartilage by Recombinant Lubricin," 53rd Annual Meeting of the Orthopaedic Research Society, Poster No: 0550, Feb. 2007. Poster 550 at the 53 annual meeting of the Orthopaedic Research Foundation, Feb. 2007.

Foulks, 2006, "Pharmacological Management of Dry Eye in the Elderly Patient," Therapy in Practice, 25(2):105-118.

SEQUENCE LISTING

<160> NUMBER OF SEQ ID NOS: 4

<210> SEQ ID NO 1
<211> LENGTH: 1404
<212> TYPE: PRT
<213> ORGANISM: Homo sapiens

<400> SEQUENCE: 1

Met Ala Trp Lys Thr Leu Pro Ile Tyr Leu Leu Leu Leu Leu Ser Val
1               5                   10                  15

Phe Val Ile Gln Gln Val Ser Ser Gln Asp Leu Ser Ser Cys Ala Gly
            20                  25                  30

```
Arg Cys Gly Glu Gly Tyr Ser Arg Asp Ala Thr Cys Asn Cys Asp Tyr
         35                  40                  45

Asn Cys Gln His Tyr Met Glu Cys Cys Pro Asp Phe Lys Arg Val Cys
 50                  55                  60

Thr Ala Glu Leu Ser Cys Lys Gly Arg Cys Phe Glu Ser Phe Glu Arg
 65                  70                  75                  80

Gly Arg Glu Cys Asp Cys Asp Ala Gln Cys Lys Lys Tyr Asp Lys Cys
                 85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Pro Asn Lys Lys Lys
        130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Arg Lys Ile Lys Ser Ser Lys Asn Ser Ala Ala Asn Arg
        180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
    290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
        355                 360                 365

Thr Thr Ile Lys Ser Ala Pro Thr Thr Pro Lys Glu Pro Ala Pro Thr
    370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Glu Pro Ala Pro Thr Thr Lys Ser Ala Pro Thr Thr Pro
            420                 425                 430

Lys Glu Pro Ala Pro Thr Thr Pro Lys Lys Pro Ala Pro Thr Thr Pro
        435                 440                 445
```

-continued

```
Lys Glu Pro Ala Pro Thr Thr Pro Lys Glu Pro Thr Pro Thr Pro
450                 455                 460

Lys Glu Pro Ala Pro Thr Thr Lys Glu Pro Ala Pro Thr Thr Pro Lys
465                     470                 475                 480

Glu Pro Ala Pro Thr Ala Pro Lys Lys Pro Ala Pro Thr Thr Pro Lys
                485                 490                 495

Glu Pro Ala Pro Thr Thr Pro Lys Glu Pro Ala Pro Thr Thr Thr Lys
                500                 505                 510

Glu Pro Ser Pro Thr Thr Pro Lys Glu Pro Ala Pro Thr Thr Thr Lys
                515                 520                 525

Ser Ala Pro Thr Thr Thr Lys Glu Pro Ala Pro Thr Thr Thr Lys Ser
530                 535                 540

Ala Pro Thr Thr Pro Lys Glu Pro Ser Pro Thr Thr Lys Glu Pro
545                 550                 555                 560

Ala Pro Thr Thr Pro Lys Glu Pro Ala Pro Thr Pro Lys Lys Pro
545                 565                 570                 575

Ala Pro Thr Thr Pro Lys Glu Pro Ala Pro Thr Pro Lys Glu Pro
                580                 585                 590

Ala Pro Thr Thr Lys Lys Pro Ala Pro Thr Pro Lys Glu Pro
                595                 600                 605

Ala Pro Thr Thr Pro Lys Glu Thr Ala Pro Thr Pro Lys Lys Leu
610                 615                 620

Thr Pro Thr Thr Pro Glu Lys Leu Ala Pro Thr Pro Glu Lys Pro
625                 630                 635                 640

Ala Pro Thr Thr Pro Glu Glu Leu Ala Pro Thr Thr Pro Glu Glu Pro
                645                 650                 655

Thr Pro Thr Thr Pro Glu Glu Pro Ala Pro Thr Thr Pro Lys Ala Ala
                660                 665                 670

Ala Pro Asn Thr Pro Lys Glu Pro Ala Pro Thr Thr Pro Lys Glu Pro
        675                 680                 685

Ala Pro Thr Thr Pro Lys Glu Pro Ala Pro Thr Thr Pro Lys Glu Thr
        690                 695                 700

Ala Pro Thr Thr Pro Lys Gly Thr Ala Pro Thr Thr Leu Lys Glu Pro
705                 710                 715                 720

Ala Pro Thr Thr Pro Lys Lys Pro Ala Pro Lys Glu Leu Ala Pro Thr
                725                 730                 735

Thr Thr Lys Glu Pro Thr Ser Thr Thr Cys Asp Lys Pro Ala Pro Thr
        740                 745                 750

Thr Pro Lys Gly Thr Ala Pro Thr Thr Pro Lys Glu Pro Ala Pro Thr
        755                 760                 765

Thr Pro Lys Glu Pro Ala Pro Thr Thr Pro Lys Gly Thr Ala Pro Thr
        770                 775                 780

Thr Leu Lys Glu Pro Ala Pro Thr Thr Pro Lys Lys Pro Ala Pro Lys
785                 790                 795                 800

Glu Leu Ala Pro Thr Thr Thr Lys Gly Pro Thr Ser Thr Thr Ser Asp
                805                 810                 815

Lys Pro Ala Pro Thr Thr Pro Lys Glu Thr Ala Pro Thr Thr Pro Lys
        820                 825                 830

Glu Pro Ala Pro Thr Thr Pro Lys Pro Ala Pro Thr Thr Pro Glu
        835                 840                 845

Thr Pro Pro Pro Thr Thr Ser Glu Val Ser Thr Pro Thr Thr Lys
850                 855                 860

Glu Pro Thr Thr Ile His Lys Ser Pro Asp Glu Ser Thr Pro Glu Leu
```

-continued

```
                865                 870                 875                 880
Ser Ala Glu Pro Thr Pro Lys Ala Leu Glu Asn Ser Pro Lys Glu Pro
                    885                 890                 895

Gly Val Pro Thr Thr Lys Thr Pro Ala Ala Thr Lys Pro Glu Met Thr
                900                 905                 910

Thr Thr Ala Lys Asp Lys Thr Glu Arg Asp Leu Arg Thr Thr Pro
            915                 920                 925

Glu Thr Thr Thr Ala Ala Pro Lys Met Thr Lys Glu Thr Ala Thr Thr
        930                 935                 940

Thr Glu Lys Thr Thr Glu Ser Lys Ile Thr Ala Thr Thr Gln Val
945                 950                 955                 960

Thr Ser Thr Thr Thr Gln Asp Thr Thr Pro Phe Lys Ile Thr Leu
                    965                 970                 975

Lys Thr Thr Thr Leu Ala Pro Lys Val Thr Thr Thr Lys Thr Ile
                980                 985                 990

Thr Thr Thr Glu Ile Met Asn Lys Pro Glu Glu Thr Ala Lys Pro Lys
            995                 1000                1005

Asp Arg Ala Thr Asn Ser Lys Ala Thr Thr Pro Lys Pro Gln Lys
    1010                1015                1020

Pro Thr Lys Ala Pro Lys Lys Pro Thr Ser Thr Lys Lys Pro Lys
    1025                1030                1035

Thr Met Pro Arg Val Arg Lys Pro Lys Thr Thr Pro Thr Pro Arg
    1040                1045                1050

Lys Met Thr Ser Thr Met Pro Glu Leu Asn Pro Thr Ser Arg Ile
    1055                1060                1065

Ala Glu Ala Met Leu Gln Thr Thr Thr Arg Pro Asn Gln Thr Pro
    1070                1075                1080

Asn Ser Lys Leu Val Glu Val Asn Pro Lys Ser Glu Asp Ala Gly
    1085                1090                1095

Gly Ala Glu Gly Glu Thr Pro His Met Leu Leu Arg Pro His Val
    1100                1105                1110

Phe Met Pro Glu Val Thr Pro Asp Met Asp Tyr Leu Pro Arg Val
    1115                1120                1125

Pro Asn Gln Gly Ile Ile Ile Asn Pro Met Leu Ser Asp Glu Thr
    1130                1135                1140

Asn Ile Cys Asn Gly Lys Pro Val Asp Gly Leu Thr Thr Leu Arg
    1145                1150                1155

Asn Gly Thr Leu Val Ala Phe Arg Gly His Tyr Phe Trp Met Leu
    1160                1165                1170

Ser Pro Phe Ser Pro Pro Ser Pro Ala Arg Arg Ile Thr Glu Val
    1175                1180                1185

Trp Gly Ile Pro Ser Pro Ile Asp Thr Val Phe Thr Arg Cys Asn
    1190                1195                1200

Cys Glu Gly Lys Thr Phe Phe Phe Lys Asp Ser Gln Tyr Trp Arg
    1205                1210                1215

Phe Thr Asn Asp Ile Lys Asp Ala Gly Tyr Pro Lys Pro Ile Phe
    1220                1225                1230

Lys Gly Phe Gly Gly Leu Thr Gly Gln Ile Val Ala Ala Leu Ser
    1235                1240                1245

Thr Ala Lys Tyr Lys Asn Trp Pro Glu Ser Val Tyr Phe Phe Lys
    1250                1255                1260

Arg Gly Gly Ser Ile Gln Gln Tyr Ile Tyr Lys Gln Glu Pro Val
    1265                1270                1275
```

```
Gln Lys Cys Pro Gly Arg Arg Pro Ala Leu Asn Tyr Pro Val Tyr
    1280                1285            1290

Gly Glu Thr Thr Gln Val Arg Arg Arg Phe Glu Arg Ala Ile
    1295            1300            1305

Gly Pro Ser Gln Thr His Thr Ile Arg Ile Gln Tyr Ser Pro Ala
    1310            1315            1320

Arg Leu Ala Tyr Gln Asp Lys Gly Val Leu His Asn Glu Val Lys
    1325            1330            1335

Val Ser Ile Leu Trp Arg Gly Leu Pro Asn Val Val Thr Ser Ala
    1340            1345            1350

Ile Ser Leu Pro Asn Ile Arg Lys Pro Asp Gly Tyr Asp Tyr Tyr
    1355            1360            1365

Ala Phe Ser Lys Asp Gln Tyr Tyr Asn Ile Asp Val Pro Ser Arg
    1370            1375            1380

Thr Ala Arg Ala Ile Thr Thr Arg Ser Gly Gln Thr Leu Ser Lys
    1385            1390            1395

Val Trp Tyr Asn Cys Pro
    1400

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatgcagggt accccaaa                                                 18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagactttgg ataaggtctg cc                                            22

<210> SEQ ID NO 4
<211> LENGTH: 7
<212> TYPE: PRT
<213> ORGANISM: Homo sapiens

<400> SEQUENCE: 4

Lys Glu Pro Ala Pro Thr Thr
1               5
```

THERAPEUTIC MODULATION OF OCULAR SURFACE LUBRICATION

CROSS-REFERENCE TO RELATED APPLICATIONS

This patent application is a divisional of U.S. application Ser. No. 12/940,425 filed Nov. 5, 2010, now allowed, which is a continuation of PCT Application No. PCT/US09/043015, filed May 6, 2009, which claims priority benefit of U.S. Provisional Application No. 61/051,112 filed May 7, 2008, each of which is incorporated herein by reference in their entireties.

FIELD OF THE INVENTION

The present invention relates to the management of ocular lubrication. In particular, the present invention relates to pharmaceutical compositions, and method of use thereof, for treating diseases associated with compromised lubrication at the corneal and conjunctival surfaces.

BACKGROUND

The proteoglycan 4 (prg4) gene encodes for highly glycosylated proteins termed megakaryocyte stimulating factor (MSF), lubricin, and superficial zone protein (SZP) (1). These molecules are collectively referred to as PRG4 or PRG4 proteins. PRG4 is present in synovial fluid and at the surface of synovium (2), tendon (3), and meniscus (4) and is suspected as being an important component for healthy synovial joints. See, e.g., (5), (6).

In tissues such as synovial joints, physicochemical modes of lubrication have been classified as fluid film or boundary. The operative lubrication modes depend on the normal and tangential forces on the articulating tissues, on the relative rate of tangential motion between these surfaces, and on the time history of both loading and motion. The friction coefficient, $\mu$, provides a quantitative measure, and is defined as the ratio of tangential friction force to the normal force. One type of fluid-mediated lubrication mode is hydrostatic. At the onset of loading and typically for a prolonged duration, the interstitial fluid within cartilage becomes pressurized, due to the biphasic nature of the tissue; fluid may also be forced into the asperities between articular surfaces through a weeping mechanism. Pressurized interstitial fluid and trapped lubricant pools may therefore contribute significantly to the bearing of normal load with little resistance to shear force, facilitating a very low $\mu$. Also, at the onset of loading and/or motion, squeeze film, hydrodynamic, and elastohydrodynamic types of fluid film lubrication occur, with pressurization, motion, and deformation acting to drive viscous lubricant from and/or through the gap between two surfaces in relative motion.

The relevant extent to which fluid pressure/film versus boundary lubrication occurs classically depends on a number of factors (13). When lubricant film can flow between the conforming sliding surfaces, which can deform elastically, elastohydrodynamic lubrication occurs. Pressure, surface roughness, and relative sliding velocity determine when full fluid lubrication begins to break down and the lubrication enters new regimes. As velocity decreases further, lubricant films adherent to the articulating surfaces begin to contribute and a mixed regime of lubrication occurs. If the velocity decreases even further and only an ultra-thin lubricant layer composed of a few molecules remain, boundary lubrication occurs. A boundary mode of lubrication is therefore indicated by a friction coefficient (ratio of the measured frictional force between two contacting surfaces in relative motion to the applied normal force) during steady sliding being invariant with factors that influence formation of a fluid film, such as relative sliding velocity and axial load (14). For articular cartilage, it has been concluded boundary lubrication is certain to occur, although complemented by fluid pressurization and other mechanisms (15-18).

In boundary lubrication, load is supported by surface-to-surface contact, and the associated frictional properties are determined by lubricant surface molecules. This mode has been proposed to be important because the opposing cartilage layers make contact over ~10% of the total area, and this may be where most of the friction occurs (19). Furthermore, with increasing loading time and dissipation of hydrostatic pressure, lubricant-coated surfaces bear an increasingly higher portion of the load relative to pressurized fluid, and consequently, this mode can become increasingly dominant (13, 20). Boundary lubrication, in essence, mitigates stick-slip (13), and is therefore manifest as decreased resistance both to steady motion and the start-up of motion. The latter situation is relevant to load bearing articulating surfaces after prolonged compressive loading (e.g., sitting or standing in vivo) (21). Typical wear patterns of cartilage surfaces (22) also suggest that boundary lubrication of articular cartilage is critical to the protection and maintenance of the articular surface structure.

With increasing loading time and dissipation of hydrostatic pressure, lubricant-coated surfaces bear an increasingly higher portion of the load relative to pressurized fluid, and consequently, $\mu$ can become increasingly dominated by this mode of lubrication. A boundary mode of lubrication is indicated by values of $\mu$ during steady sliding being invariant with factors that influence formation of a fluid film, such as relative sliding velocity and axial load. Boundary lubrication, in essence, mitigates stickslip, and is therefore manifest as decreased resistance both to steady motion and the start-up of motion.

The precise mechanisms of boundary lubrication at biological interfaces are currently unknown. However, proteoglycan 4 (PRG4) may play a critical role as a boundary lubricant in articulating joints. This secreted glycoprotein is thought to protect cartilaginous surfaces against frictional forces, cell adhesion and protein deposition. Various native and recombinant lubricin proteins and isoforms have been isolated and characterized. For instance, U.S. Pat. Nos. 5,326,558; 6,433,142; 7,030223, and 7,361,738 disclose a family of human megakaryocyte stimulating factors (MSFs) and pharmaceutical compositions containing one or more such MSFs for treating disease states or disorders, such as a deficiency of platelets. U.S. Pat. Nos. 6,960,562 and 6,743,774 also disclose a lubricating polypeptide, tribonectin, comprising a substantially pure fragment of MSF, and methods of lubricating joints by administering tribonectin systemically or directly to tissues.

A challenge to boundary lubrication is the presence of inflammation in surrounding tissues, as well as increased protease levels in the synovial fluid. Loss of the boundary-lubricating ability of synovial fluid after injury is associated with damage to the articular cartilage matrix. This can be attributed to inflammatory processes resulting from the injury, particularly in the early phases. Another challenge to boundary lubrication is a sex steroid imbalance, especially in arthritic disorders such as rheumatoid arthritis. Sex steroids are involved in the pathogenesis and regulation of inflammation in rheumatoid arthritis, a disease characterized by chronic inflammatory synovitis. Androgens suppress, whereas estrogens promote, inflammatory processes. Consequently, the relative levels of androgens and estrogens in the synovial environment are extremely important in determining the progression of inflammation (7, 8, 23). Various androgen compounds reduce the magnitude of lymphocyte infiltration in lacrimal tissue. See, e.g., U.S. Pat. Nos. 5,620,921; 5,688,765; 5,620,921; and 6,107,289.

SUMMARY OF THE INVENTION

The present invention provides, in various embodiments, pharmaceutical compositions, and methods of use thereof, for managing ocular lubrication, including the therapeutic replenishment and enrichment of boundary lubricant molecules at the ocular surface.

The present invention provides the discovery that PRG4 mRNA is expressed in human corneal and conjunctival epithelial cells, as well as in mouse lacrimal and meibomian glands, indicating that PRG4 protein is presented in these tissues on the ocular surface. In addition, PRG4 protein serves to protect the cornea and conjunctiva against significant shear forces generated during an eyelid blink, contact lens wear, and other undesirable conditions. The impact of the tear film, including the impact of inflammation, proinflammatory cytokines, sex steroid imbalance and proteases on the composition and function of the films, provide a course of therapy for ocular tissues which promotes boundary lubrication.

In certain embodiments, the present invention provides a pharmaceutical composition suitable for topical application to an ocular surface comprising a therapeutically effective concentration of a PRG4 inducing compound. In certain embodiments, the pharmaceutical composition further comprises an ophthalmically acceptable agent that increases the residence time of the PRG4 inducing compound on the ocular surface. In further or alternative embodiments, a pharmaceutical composition described herein comprises a PRG4 inducing compound in combination with a therapeutically effective concentration of PRG4. The PRG4 inducing compounds encompassed in the present invention include, but are not limited to, an androgen, an androgen analogue, a selective androgen receptor modulator, a selective estrogen receptor modulator, an estrogen antagonist, an aromatase inhibitor, an antiprotease, a proinflammatory cytokine antagonist, a cytokine release inhibitor, an antiinflammatory cytokine, an anti-inflammatory agent, a NF-κ-B inhibitor, and a proteasome inhibitor. Described in certain instances of the present invention is the observation that PRG4 expression in corneal and conjunctival epithelial cells is upregulated by the PRG4 inducing compounds, as discussed above, thus, providing synergistic protection of cornea and conjunctiva against significant shear forces with PRG4.

In certain embodiments, the androgen analogues include, but are not limited to 17α-methyl-17β-hydroxy-2-oxa-5α-androstan-3-one derivative, a nitrogen-substituted androgen, a testosterone derivative, a 4,5α-dihydrotestosterone derivative, a 19-nortestosterone derivative, a 17β-hydroxy-5α-androstane derivative containing a ring A unsaturation, or a structural subclass of androgens comprising androgenic compounds with unusual structural features.

In some embodiments, the selective androgen receptor modulators (SARMs) include, but are not limited to, arylpropionamide compound, such as S-3-(4-acetylamino-phenoxy)-2-hydroxy-2-methyl-N-(4-nitro-3-trifluoromethyl-phenyl)-propionamide[S-4], or S-3-(4-fluorophenoxy)-2-hydroxy-2-methyl-N-(4-nitro-3-trifluoromethyl-phenyl)-propionamide[S-1]), bicyclic hydantoin, quinoline, tetrahydroquinoline, and analogues thereof, that have in vivo androgenic and anabolic activity of a non-steroidal ligand for the androgen receptor.

In certain embodiments, the selective estrogen receptor modulators (SERMs) include, but are not limited to, non-steroidal ligands of the estrogen receptor that are capable of inducing a number of conformational changes in the receptor and thereby eliciting a variety of distinct biological profiles (e.g. prevention of estrogen-induced inflammation), and estrogen antagonists (steroidal, non-steroidal) irregardless of receptor affinity. In certain embodiments, the PRG4 inducing compounds also include aromatase inhibitors, antiproteases, pro-inflammatory cytokine antagonists, such as an anti-TNFα antibody, a soluble TNFα receptor, or an IL-1 receptor antagonist, cytokine release inhibitors, NF-κ-B inhibitors, cytokines (e.g. TGF-β), anti-inflammatory agents, such as cyclosporine A, omega 3 and 6 fatty acids, or proteasome inhibitors.

In certain embodiments, the pharmaceutical composition of the present invention comprises a therapeutically effective concentration of a PRG4 inducing compound in the range of about 0.0001-0.1% w/v, in combination with a therapeutically effective concentration of PRG4 in the range of about 10-10,000 μg/mL. In certain embodiments, the pharmaceutical composition of the present invention further comprises a therapeutically effective concentration of one or more hyaluronic acid or salts thereof, in the range of about 10-100,000 μg/mL. In certain embodiments, the pharmaceutical composition of the present invention further comprises a therapeutically effective concentration of one or more surface active phospholipids, such as L-α-dipalmitoylphosphatidylcholine (DPPC), phosphatidylcholine (PC), phosphatidylethanolamine (PE), sphingomyelin (Sp), neutral or polar lipids, in the range of about 10-10,000 μg/mL. The present invention provides that the combinations of a PRG4 inducing compound and PRG4, and other modulators or boundary lubricant molecules allow the direct transport of PRG4 and other boundary lubricant molecules to the ocular surface cells, where the PRG4 and boundary lubricant molecules tend to aggregate, and provide a pharmaceutically efficient carrier to the cornea and conjunctiva for efficient modulation of boundary lubrication.

In certain embodiments, the pharmaceutical compositions described herein comprise a residence-time increasing agent that increases the residence time of the PRG4 inducing compound on the ocular surface. In some embodiments, the residence-time-increasing agent is present in an amount such that when the pharmaceutical composition is administered to the surface of an eye of an individual, a therapeutically effective amount of a PRG4 inducing compound described herein is retained upon the surface of the eye. In certain embodiments, the residence-time-increasing agent is selected and/or is present in an amount such that the therapeutically effective amount of the PRG4 inducing compound is retained on the surface of the eye for any therapeutically effective period of time, at least 1 minute, at least 2 minutes, at least 5 minutes, at least 10 minutes, at least 15 minutes, at least 20 minutes, at least 30 minutes, at least 1 hour, or more. In certain embodiments, ophthalmically acceptable residence-time increasing agents or mucoadhesives may include, by way of non-limiting example, hydroxypropylmethylcellulose, carboxymethylcellulose, carbomer (acrylic acid polymer), poly(methylmethacrylate), polyacrylamide, polycarbophil, polyethylene oxide, acrylic acid/butyl acrylate copolymer, sodium alginate, dextran, or combinations thereof. The present invention encompasses any high molecular weight polymers that would increase the time that the PRG4 inducing compound remains on the surface of the eye.

The pharmaceutical composition of the present invention may also comprise one or more ophthalmically acceptable agents selected from the group consisting of an ophthalmically acceptable demulcent, ophthalmically acceptable excipient, ophthalmically acceptable astringent, ophthalmically acceptable vasoconstrictor, and ophthalmically acceptable emollient.

Exemplary ophthalmically acceptable demulcents contemplated in the present invention include, but are not limited to, carboxymethylcellulose sodium (e.g., about 0.2 to 2.5% w/v), hydroxyethyl cellulose (e.g., about 0.2 to 2.5% w/v), hypromellose (e.g., about 0.2 to 2.5% w/v), methylcellulose (e.g., about 0.2 to 2.5% w/v), dextran 70 (e.g., about 0.1% w/v), gelatin (e.g., about 0.01% w/v), glycerin (e.g., about 0.2 to 1% w/v), polyethylene glycol 300 (e.g., about 0.2 to 1% w/v), polyethylene glycol 400 (e.g., about 0.2 to 1% w/v), polysorbate 80 (e.g., about 0.2 to 1% w/v), propylene glycol (e.g., about 0.2 to 1% w/v), polyvinyl alcohol (e.g., about 0.1 to 4% w/v), povidone (e.g., about 0.1 to 2% w/v). Exemplary ophthalmically acceptable excipients/emollients contemplated in the present invention include, but are not limited to, anhydrous lanolin (e.g., about 1 to 10% w/v), lanolin (e.g., about 1 to 10% w/v), light mineral oil (e.g., ≤about 50% w/v), mineral oil (e.g., ≤about 50% w/v), paraffin (e.g., ≤about 5% w/v), petrolatum (e.g., ≤about 100% w/v), white ointment (e.g., ≤about 100% w/v), white petrolatum (e.g., ≤about 100% w/v), white wax (e.g., ≤about 5% w/v), yellow wax (e.g., ≤about 5% w/v). An exemplary ophthalmically acceptable astringent contemplated in the present invention includes, but is not limited to, zinc sulfate (e.g., about 0.25% w/v). Exemplary ophthalmically acceptable vasoconstrictors contemplated in the present invention include, but are not limited to, ephedrine hydrochloride (e.g., about 0.123% w/v), naphazoline hydrochloride (e.g., about 0.01 to about 0.03% w/v), phenylephrine hydrochloride (e.g., about 0.08 to about 0.2% w/v), and tetrahydrozoline hydrochloride (e.g., about 0.01 to about 0.05% w/v).

In some of these embodiments, the demulcents, excipients, astringents, vasoconstrictors, emollients and electrolytes provide a means to deliver the PRG4 inducing compound and the PRG4 protein in an ophthalmically acceptable manner. Ophthalmically acceptable compositions are suitable for topical application to the ocular surface if they lack unacceptable eye toxicity, burning, itchiness, viscosity, blurred vision, etc. upon application.

In certain embodiments, the present invention provides a pharmaceutical composition suitable for topical application to an ocular surface comprising a therapeutically effective concentration of a PRG4 inducing compound and PRG4 protein suspended in a phosphate buffered saline solution or an ophthalmically acceptable balanced salt solution comprising tear electrolytes, which include, but are not limited to, sodium chloride (e.g., about 44%-54% mole fraction), potassium chloride (e.g., about 8%-14% mole fraction), sodium bicarbonate (e.g., about 8%-18% mole fraction), potassium bicarbonate (e.g., about 0%-4% mole fraction), calcium chloride (e.g., about 0%-4% mole fraction), magnesium chloride (e.g., about 0%-4% mole fraction), trisodium citrate (e.g., about 0%-4% mole fraction), hydrochloric acid (e.g., about 0%-20% mole fraction) or sodium hydroxide (e.g., about 0%-20% mole fraction). In one embodiment, the carrier could be formulated to generate an aqueous electrolyte solution in the 150-200 mM range.

In certain embodiments, the present invention provides a pharmaceutical composition suitable for topical application to an ocular surface comprising a therapeutically effective concentration of a PRG4 inducing compound and PRG4 suspended in an ophthalmically acceptable balanced salt solution comprising at least three electrolytes, including but not limited to, sodium chloride (NaCl) 0.64%, potassium chloride (KCl) 0.075%, calcium chloride dihydrate ($CaCl_2.2H_2O$) 0.048%, magnesium chloride hexahydrate ($MgCl_2.6H_2O$) 0.03%, sodium acetate trihydrate ($C_2H_3NaO_2.3H_2O$) 0.39%, sodium citrate dehydrate ($C_6H_5Na_3O_7.2H_2O$) 0.17%, sodium hydroxide and/or hydrochloric acid (to adjust pH to approximately 7.5) with an osmolarity of approximately 300 mOsms/L.

In certain embodiments, the present invention provides a pharmaceutical composition suitable for topical application to an ocular surface comprising a therapeutically effective concentration of a PRG4 inducing compound and PRG4 suspended in an ophthalmically acceptable balanced salt solution, comprised of sodium ($Na^+$) of approximately 128 mM, potassium ($K^+$) of approximately 24 mM, chloride ($Cl^-$) of approximately 113 mM, calcium ($Ca^{2+}$) of approximately 0.4 mM, magnesium ($Mg^{2+}$) of approximately 0.3 mM, $HCO_3^-$ of approximately 5 mM, citrate of approximately 1 mM, phosphate of approximately 14 mM, acetate of approximately 15 mM, and sodium hydroxide and/or hydrochloric acid (to adjust pH to approximately 7.5) with an osmolarity of approximately 300 mOsms/L.

The present invention further provides a method for treating ocular lubrication deficiency, or symptoms associated therewith, in an individual in need. The method comprises topically administering to the ocular surface of the individual in need any pharmaceutical composition described herein. In some embodiments, the pharmaceutical composition is one comprising a therapeutically effective concentration of a PRG4 inducing compound and a PRG4 protein. In further or alternative embodiments, the pharmaceutical composition is one comprising a therapeutically effective concentration of a PRG4 inducing compound and an ophthalmically acceptable residence-time increasing agent. In certain embodiments, the pharmaceutical composition, e.g., one comprising the PRG4 inducing compound and the PRG4 protein, is administered in combination with an ophthalmically acceptable formulation comprising one or more ophthalmically acceptable agents selected from the group consisting of an ophthalmically acceptable demulcent, ophthalmically acceptable excipient, ophthalmically acceptable astringent, ophthalmically acceptable vasoconstrictor, and ophthalmically acceptable emollient.

In some embodiments, the pharmaceutical composition, e.g., a composition comprising the PRG4 inducing compound and an ophthalmically acceptable mucoadhesive agent and/or the PRG4 protein, is administered in combination with an ophthalmically acceptable solution comprising a therapeutically effective concentration of sodium hyaluronate or hyaluronic acid, or a surface active phospholipid, as discussed above. In certain embodiments, the pharmaceutical composition comprising the PRG4 inducing compound and the PRG4 protein is administered in combination with a phosphate buffered saline solution or an ophthalmically acceptable balanced salt solution comprising one or more electrolytes, as discussed above.

In some embodiments, the present invention provides a method for treating a deficiency in ocular lubrication or symptoms associated therewith (e.g., dry eye), due to tear loss or unstable tear film in the ocular boundary loop, such as androgen deficiency, Sjögren's syndrome and keratoconjunctivitis sicca (KCS). Such method comprises topically administering to the ocular surface of an individual in need the pharmaceutical composition of the present invention.

In certain embodiments, the present invention further provides a method for addressing and treating the conditions associated with ocular lubrication, including unfavorable or deficient ocular lubrication. Exemplary conditions include, but are not limited to, aqueous or evaporative dry eye disease, Sjögren's syndrome, keratoconjunctivitis sicca, androgen deficiency, meibomian gland disease, estrogen replacement therapy, contact lens wear, refractive surgery, allergy, reduced tear film breakup time, allergy, ocular surface disorders, increased protease levels in the tear film and at the ocular surface, chronic inflammation, hyperosmolarity, and aging.

The present invention also provides, in certain embodiments, a method of locally inducing PRG4 on an ocular surface comprising topically administering to the ocular surface of an individual in need thereof a therapeutically effective amount of any pharmaceutical composition of the present invention, e.g., a composition comprising a PRG4 inducing compound and PRG4 and/or an ophthalmically acceptable mucoadhesive agent. In certain embodiments, provided herein is a method of locally inducing PRG4 on an ocular surface comprising topically administering to the ocular surface of an individual in need thereof a therapeutically effective amount of any pharmaceutical composition described herein, a therapeutically effective amount of a PRG4 inducing compound being retained on the ocular surface for a therapeutically effective period of time.

DETAILED DESCRIPTION OF THE INVENTION

Figure 1:
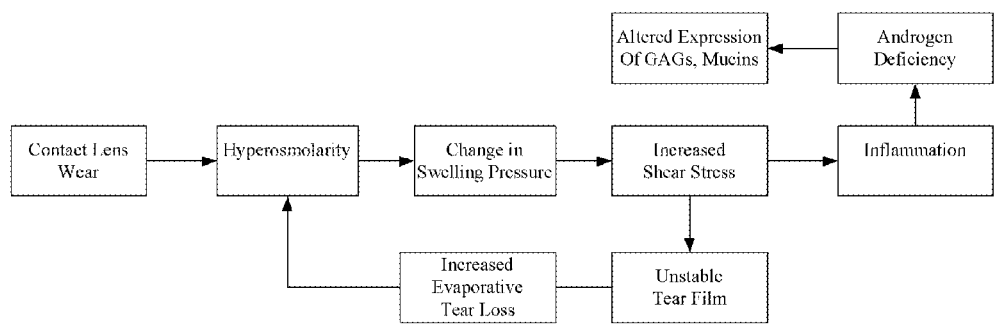
FIG. 1 represents feedback loops within ocular surface boundary lubrication.
Figure 2:
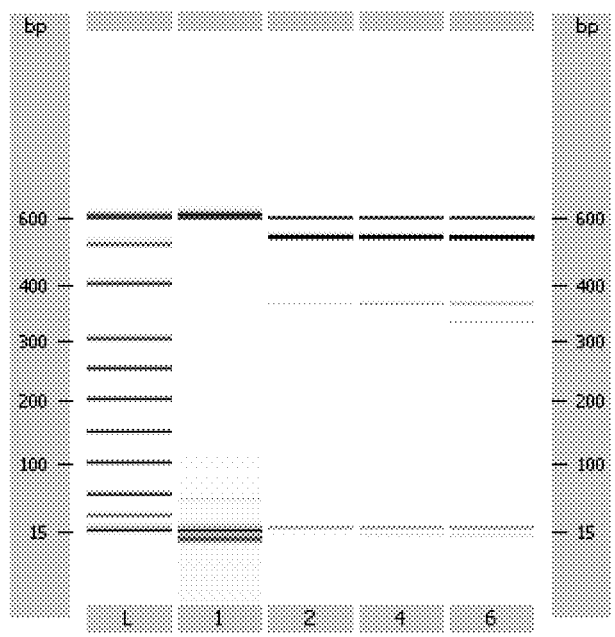
FIG. 2 illustrates PRG4 mRNA expression in human corneal epithelial cells. Human corneal epithelial cells were isolated from the corneoscleral rims of male and female donors. Amplified samples were screened for the presence of PRG4 products by using an Agilent 2100 Bioanalyzer. Vertical lanes contain: L. MW ladder; 1. No template control; 2. Corneal tissue from a 33-year female; 4. Cultured corneal epithelial cells from a 70-year female; 6. Cultured corneal epithelial cells from a 53-year male.
Figure 3:
FIG. 3 illustrates PRG4 mRNA expression in human conjunctival epithelial cells. Human corneal epithelial cells were isolated from the corneoscleral rims of male and female donors. Amplified samples were screened for the presence of PRG4 products by using agarose gel electrophoresis. Vertical lanes contain: 1. MW ladder; 2. No template control; 4. Human female conjunctiva; 5. Human male conjunctiva.
Figure 4:
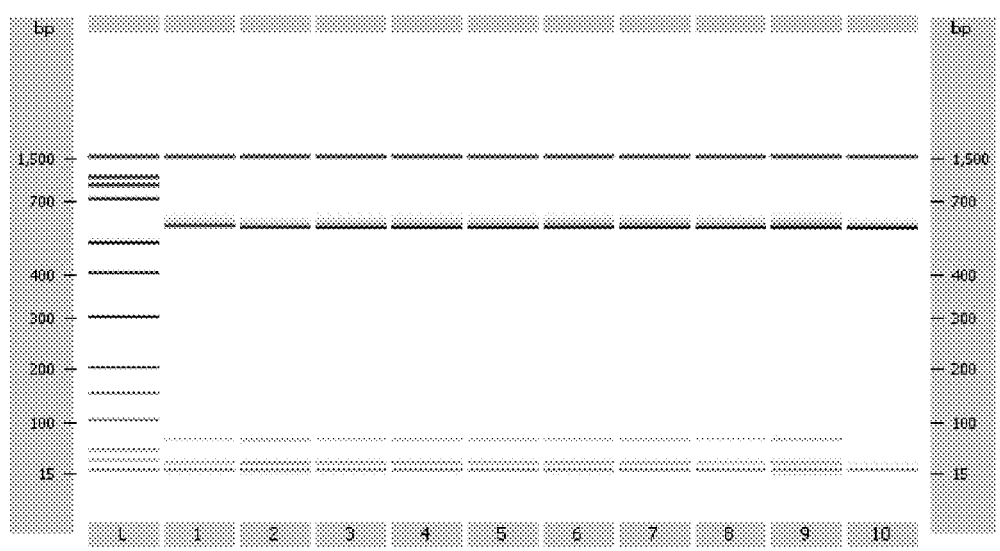
FIG. 4 illustrates PRG4 mRNA expression in human conjunctival impression cytology samples. Conjunctival impression cytology samples were isolated from male and female donors. Amplified samples were screened for the presence of PRG4 products by using an Agilent 2100 Bioanalyzer. Vertical lanes contain: L. MW ladder; 1-9. Conjunctival impression cytology samples; 10. Repeat of human conjunctival epithelial cells (Lane 4 in FIG. 3).
Figure 5:
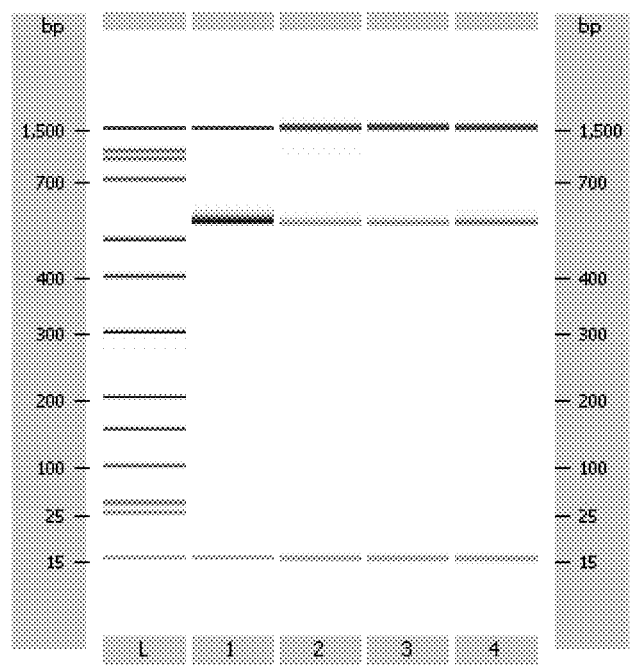
FIG. 5 illustrates PRG4 mRNA expression in human corneoscleral rim tissue samples. L. Human corneal epithelial cells were isolated from the corneoscleral rims of male and female donors. Amplified samples were screened for the presence of PRG4 products by using an Agilent 2100 Bioanalyzer. Vertical lanes contain: MW ladder; 1. Human liver cDNA standard; 2. Corneoscleral rim tissue from a 24-year female; 3. Corneoscleral rim tissue from a 51-year female; 4. Human conjunctival epithelial cells.

Provided in certain embodiments herein, are compositions methods for treating ocular lubrication deficiency (e.g., ocular boundary lubrication deficiency), or symptoms associated therewith, in an individual in need thereof comprising topically administering to the ocular surface of the individual a pharmaceutical composition comprising a therapeutically effective concentration of a PRG4 inducing compound. In specific embodiments, the PRG4 inducing compound is in combination with PRG4. In further or alternative embodiments, the PRG4 inducing compound is in combination with an ophthamically acceptable residence-time increasing agent (e.g., an agent that extends the period in which the PRG4 inducing compound and/or PRG4 remain therapeutically available in the eye). Provided in specific embodiments herein are pharmaceutical compositions comprising a PRG4 inducing compound and PRG4 in an ophthalmically acceptable formulation. In some specific embodiments, provided herein is a pharmaceutical composition suitable for topical application to an ocular surface comprising a therapeutically effective concentration of a PRG4 inducing compound (e.g., in combination with PRG4) suspended in a phosphate buffered solution or an ophthalmically acceptable balanced salt solution, and may also be in combination with one or more ophthalmically acceptable agents or carriers selected from the group consisting of an ophthalmically acceptable demulcent, an ophthalmically acceptable excipient, an ophthalmically acceptable astringent, an ophthalmically acceptable vasoconstrictor, an ophthalmically acceptable emollient, hyaluronic acid, sodium hyaluronate, and surface active phospholipids.

Provided in some embodiments herein are pharmaceutical compositions, and methods of use thereof, for treating a deficiency in ocular lubrication at the ocular surface (e.g., a deficiency of, such as decreased or undesirable, ocular boundary lubrication). A pharmaceutical composition of certain embodiments of the present invention comprises a PRG4 inducing compound in combination with an isolated or purified PRG4 protein suspended in a phosphate buffered solution or an ophthalmically acceptable balanced salt solution, and further may also be in combination with one or more ophthalmic agents selected from the group consisting of an ophthalmic demulcent, excipient, astringent, vasoconstructor, and emollient. In some embodiments, any pharmaceutical composition provided herein may further comprise one or more additional therapeutic agents selected from the group consisting of sodium hyaluronate, surface active phospholipids, and electrolytes in a pharmaceutically acceptable carrier for topical administration.

The present invention provides, in certain embodiments, a pharmaceutical composition for managing decreased ocular boundary lubrication by upregulating boundary lubricant expression at the ocular surface. In certain embodiments, the pharmaceutical composition upregulates PRG4 production by a PRG4 inducing compound. In certain instances, the upregulation of PRG4 expression is specifically localized at the ocular surface (acting on the conjunctival and corneal epithelium, goblet cells, etc.) and does not require modulation of other ocular tissues such as the lacrimal or meibomian gland.

As used herein, a "PRG4 inducing compound" or "PRG4 inducer" refers to a compound that increases the concentration of PRG4, e.g., a compound that is capable of upregulating PRG4 expression, promoting the biosynthesis of PRG4, inhibiting the degradation of PRG4, or the like, including but not limited to, an androgen or androgen analogue, selective androgen receptor modulator, selective estrogen receptor modulator, estrogen antagonist, aromatase inhibitor, antiprotease, proinflammatory cytokine antagonist (e.g. selected from the group consisting of anti-TNF$\alpha$ antibody, soluble TNF$\alpha$ receptor, and IL-1 receptor antagonist), cytokine release inhibitor, antiinflammatory cytokine (e.g. TGF-$\beta$), antiinflammatory agent (e.g. cyclosporine A, c-Jun N-terminal (JNK) kinase inhibitor, extracellular-signal regulated kinase (ERK) inhibitor, mitogen-activated protein (MAP) kinase inhibitor, and matrix metalloproteinase (MMP) inhibitor, omega 3 and 6 fatty acids), NF-$\kappa$ B inhibitor, or proteasome inhibitor, and pharmaceutically acceptable carriers for topical use.

In yet another embodiment, the androgen or androgen analogue is selected from the group consisting of a 17$\alpha$-methyl-17$\beta$-hydroxy-2-oxa-5$\alpha$-androstan-3-one derivative, a nitrogen-substituted androgen, a testosterone derivative, is a 4,5$\alpha$-dihydrotestosterone derivative, a 19-nortestosterone derivative, a 17$\beta$-hydroxy-5$\alpha$-androstane derivative containing a ring A unsaturation, and a structural subclass of androgens comprising androgenic compounds with unusual structural features.

In another preferred embodiment, the selective androgen receptor modulators (SARMs) are selected from a group consisting of aryl-propionamide (e.g. S-3-(4-acetylamino-phenoxy)-2-hydroxy-2-methyl-N-(4-nitro-3-trifluoromethyl-phenyl)-propionamide[S-4], or S-3-(4-fluorophenoxy)-2-hydroxy-2-methyl-N-(4-nitro-3-trifluoromethyl-phenyl)-propionamide[S-1]), bicyclic hydantoin, quinoline, and tetrahydroquinoline analogues that have in-vivo androgenic and anabolic activity of a non-steroidal ligand for the androgen receptor.

In yet another preferred embodiment, the selective estrogen receptor modulators (SERMs) are non-steroidal ligands of the estrogen receptor that are capable of inducing a number of conformational changes in the receptor and eliciting a variety of distinct biologic profiles. Preferably, the SERMs are those that prevent estrogen-induced inflammation in ocular surface tissues. In certain preferred embodiments, the estrogen antagonists are steroidal or non-steroidal compounds independent of receptor affinities.

Another embodiment of the present invention provides for the methods and pharmaceutical compositions mentioned above for managing decreased ocular boundary lubrication by modulating hyperosmolarity at the ocular surface. By interrupting the feedback mechanisms which prevent secreted components from reducing friction coefficients and mitigating shear stress, the present invention includes pharmaceutical compositions for managing decreased boundary lubrication by modulating osmolarity at the ocular surface.

In another embodiment, the present invention also provides a therapeutic composition, and method of use thereof, to manage and alleviate undesirable conditions for ocular boundary lubrication by compensating for alterations in sex steroid expression at the ocular surface. Androgens inhibit aromatization in synovial cells when their concentration is sufficiently high. Testosterone antagonizes the effects of IL-1 on both proteoglycan loss and proteoglycan synthesis in cartilage. Dehydroepiandrosterone, an androgen precursor, decreases knee joint swelling during acute and chronic antigen-induced arthritis (AIA), as well as histological signs of inflammation and joint destruction during chronic AIA (9). Androgens also appear to protect cartilage from inflammation-induced breakdown. This finding supports a pathogenic role for hypoandrogenism in rheumatoid arthritis and suggests that long-term androgen replacement may help prevent joint damage and disability. Thus, in one embodiment of the invention, the proinflammatory cytokine-induced effects on sex steroid imbalance and associated inflammation at the ocular surface may be countered the by administration of androgens, selective estrogen receptor modulators, estrogen antagonists and aromatase inhibitors.

In some embodiments, the present invention also provides a pharmaceutical composition, and method of use thereof, to manage and alleviate undesirable conditions for ocular boundary lubrication, by compensating for the inflammation- and protease-induced reduction in the boundary-lubricating ability of synovial and tear fluid by the administration of factors that suppress inflammation and interfere with protease activity.

Certain embodiments of the present invention provide therapeutic compositions, and methods of use thereof, to manage and alleviate undesirable conditions for ocular boundary lubrication, such as chronic inflammation and hyperosmolarity that result from androgen deficiency, estrogen replacement therapy, contact lens wear, compromised tear film, allergy, aging, ocular surface diseases, and increased protease levels in the tear film and at the ocular surface. In one embodiment, modulation of PRG4 regulation on the ocular surface promotes favorable conditions for proper boundary lubrication by interrupting the central positive feedback loop through reduction of shear stress at the ocular surface.

It should be noted that the importance and the mechanism of ocular boundary lubrication has not heretofore been recognized within the ophthalmic community. For years, the scientific consensus within the orthopaedic research community was that hydrodynamic lubrication was by far the dominant mode of lubrication for articular cartilage, and that boundary lubrication was simply an afterthought. Moreover, those researchers studying boundary lubrication at cartilage surfaces suggest that boundary lubrication is likely only important under "high load and low velocity," which are opposite to the conditions at the ocular surface, where there are relatively low axial loads and relatively fast sliding velocities. See, e.g., (10). Moreover, boundary lubrication involving the corneal glyocalyx has not heretofore been considered. Jay et al. compared purified lubricating factor from bovine synovial fluid to "mucinous glycoprotein from human submandibular saliva and stimulated tears," and concluded "mucin secreted by the lacrimal gland did not lubricate," overlooking the possibility that the corneal epithelium was a source of lubricant or that boundary lubrication was an important contributor at the ocular surface. See, e.g., (11). The most recent mathematical models of tear film dynamics also ignore the possibility of boundary lubrication, claiming a "lubrication approximation" for the height of the tear film such that "the mucus layer on the cornea can be taken to provide a no-slip surface for the aqueous film" and that "it should be noted that the model only predicts the evolution prior to the [tear film] thickness reaching some critically thin value at which the model breaks down." See, e.g., (12).

There is a need to manage ocular lubrication and protect the cornea and conjunctiva against significant shear forces generated from the undesirable conditions described herein, including, by way of non-limiting example, aqueous or evaporative dry eye disease, Sjögren's syndrome, keratoconjunctivitis sicca, androgen deficiency, meibomian gland disease, estrogen replacement therapy, contact lens wear, refractive surgery, allergy, reduced tear film breakup time, allergy, ocular surface disorders, increased protease levels in the tear film and at the ocular surface, chronic inflammation, hyperosmolarity, and aging.

In some instances, the loading of cornea and conjunctiva is likely dominated by shear forces. In certain instances, eyelid blinking, as well as contact lens wear, generates significant stress upon ocular surface epithelial cells, and this is especially true in the presence of a compromised tear film. As shown in FIG. 1, it is suggested that increased shear stress leads to tear film instability, evaporative tear loss, hyperosmolarity, changes in swelling pressure and a feedback elevation in shear stress. In some instances, increased shear stress is also thought to promote inflammation, androgen deficiency and decreased expression of proteoglycans. In certain instances increased shear stress and its sequelae may, over time, lead to a loss of boundary lubrication at the ocular surface.

A deficiency in ocular lubrication and symptoms associated therewith can be determined by any suitable method. In some instances, a deficiency in ocular lubrication and symptoms associated therewith is defined either qualitatively (e.g., a feeling of low lubrication, dry eye, discomfort, etc.) or quantitatively (e.g., measured through mechanical, biochemical, electrical, optical or other methods of quantitative assays).

In certain instances, in undesirable conditions for ocular boundary lubrication, such those resulting from aqueous or evaporative dry eye disease, Sjögren's syndrome, keratoconjunctivitis sicca, androgen deficiency, meibomian gland disease, estrogen replacement therapy, contact lens wear, refractive surgery, allergy, reduced tear film breakup time, allergy, ocular surface disorders, increased protease levels in the tear film and at the ocular surface, chronic inflammation, hyperosmolarity, and aging, a compromised tear film will exist. In some of these situations, increased evaporation may preclude efficient fluid film lubrication, but allow boundary lubrication and a molecular sacrificial mechanism to reduce shear stress at the cell surface. Certain embodiments of the present invention provide that therapeutic regulation, replenishment and enrichment of boundary lubricant molecules at the ocular surface would interrupt the feedback loop through which the unfavorable conditions associated with a deficiency in ocular lubrication promote ocular surface distress.

In certain instances, and as provided herein, PRG4 protein plays a critical role in the eye as a boundary lubricant. In some instances, this secreted glycoprotein protects the ocular surface to protect the cornea and conjunctiva against significant shear forces generated during an eyelid blink, contact lens wear, and any other undesirable ocular boundary lubrication caused by chronic inflammation and hyperosmolarity that result from dry eye disease, androgen deficiency, estrogen replacement therapy, compromised tear film, allergy, aging, ocular surface diseases, and increased protease levels in the tear film and at the ocular surface.

In another exemplary embodiment, the present invention features a sacrificial mechanism for ocular boundary lubrication, whereby surface bound receptors reversibly bind one or more gel forming or surfactant constructs. In some instances, the gel forming or surfactant constructs detach during a shear event, thereby preventing the shear stress from reaching (or reducing the shear stress reaching) the epithelial surface. In certain embodiments, following the transient shearing event, the gel forming and surfactant constructs, allowed to return to their undisturbed equilibrium, rebind to the surface bound receptors. In some embodiments, the entire construct can detach during shear. In certain instances, the thermodynamics of this equilibrium can increase the probability of release from the receptor with increasing shear amplitude, but any one association may be easily reversible.

Any pharmaceutical composition of the present invention (e.g., a composition comprising a PRG4 inducing compound and PRG4 protein suspended in a phosphate buffered solution or an ophthalmically acceptable balanced solution) is applied topically to the ocular surface, wherein the PRG4 inducing compound upregulates PRG4 protein expression and localization on the ocular surface where the PRG4 associates, binds to, and acts as a surface bound receptor that is allowed to interact with endogenous proteins and proteoglycans within the tear film to establish a sacrificial mechanism to reduce the friction during eyelid blinks at the ocular surface, prevent protein adsorption at the ocular surface, and reduce dry spots caused by tear film instability.

In another embodiment of the current invention, any pharmaceutical composition described herein (e.g., a composition comprising a PRG4 inducing compound and a PRG4 protein) may also be in combination with one or more of hyaluronic acid and phospholipid constructs. In certain instances of this embodiment, PRG4 acts as the surface bound receptor that interacts with the exogenously supplied hyaluronic acid and/or phospholipids to establish the sacrificial mechanism to reduce the friction during eyelid blinks at the ocular surface, prevent protein adsorption at the ocular surface, and reduce dry spots caused by tear film instability. In this embodiment, the hyaluronic acid and phospholipid constructs disassociate from the PRG4 during a shear event. In yet another embodiment, the entire construct detaches during a shear event to prevent the shear stress from reaching the epithelium.

In yet another embodiment, functional fragments, multimers (e.g., dimers, trimers, tetramers, etc.), homologs or orthologs of PRG4 act as the surface receptor and/or gel forming constructs in the sacrificial mechanism. Functional fragments and homologs of PRG4 include those with a fewer repeats within the central mucin-like KEPAPTT-repeat domain, glycosylated and non-glycosylated forms of the protein, splice variants, recombinant forms, and the like. A lubricating fragment of PRG4 exhibits at least 20%, 30%, 40%, 50%, 60%, 70%, 80%, 90%, or 95% of the ophthalmic lubricating effect of human PRG4, as measured qualitatively, mechanically, optically, electrically, or by biochemical assay.

As used herein, the term "PRG4," "PRG4 protein," "proteoglycan 4," and "lubricant," are used interchangeably. PRG4 is used herein also to encompass the term megakaryocyte stimulating factor (MSF), that has been accepted for the UCL/HGNC/HUGO Human Gene Nomenclature data base, and superficial zone protein (SZP). The PRG4 or lubricin protein (used interchangeably herein with lubricin proteoglycan) as used herein refers to any isolated or purified native or recombinant lubricin proteins, homologs, functional fragments or motifs, isoforms, and/or mutants thereof. In certain embodiments, the isolated or purified PRG4 protein comprises an amino acid sequence for a human native or recombinant lubricin protein. In other embodiments, the isolated or purified PRG4 protein comprises an amino acid sequence encoded by prg4 gene exons that encode the full length PRG4 protein or isoforms' primary structures. The proteoglycan 4 (prg4) gene contains 12 exons. The PRG4 protein used herein comprises an amino acid sequence encoded by prg4 gene exons 1-12, more preferably, exons 6-12, and most preferably, exons 9-12.

As used herein, the PRG4 protein includes any PRG4 proteins now known, or later described. In certain embodiments, a preferred PRG4 protein amino acid sequence is provided in SEQ ID NO:1. The PRG4 protein shares the primary amino acid structure of any known PRG4 proteins or isoforms with at least 60% homology, preferably 75% homology, more preferably 85%, 90%, 95%, 96%, 97%, 98%, 99% or more homology. In certain embodiments, a preferred PRG4 protein has an average molar mass of between 50 kDa and 400 kDa, comprising one or more biological active portions of the PRG4 protein, or functional fragments, such as a lubricating fragment, or a homolog thereof.

As used herein, the PRG4 protein comprises a biological active portion of the protein. As used herein, a "biologically active portion" of the PRG4 protein includes a functional fragment of a protein comprising amino acid sequences sufficiently homologous to, or derived from, the amino acid sequence of the protein, which includes fewer amino acids than the full length protein, and exhibits at least one activity of the full-length protein. Typically a biologically active portion comprises a functional domain or motif with at least one activity of the protein. A biologically active portion of a protein can be a polypeptide which is, for example, 10, 25, 50, 100, 200, or more amino acids in length. In one embodiment, a biologically active portion of the PRG4 protein can be used as a therapeutic agent alone or in combination with other therapeutic agents for treating undesirable or decreased ocular boundary lubrication.

The nucleic acid and amino acid sequences of several native and recombinant PRG4 or lubricin proteins, and characterization of the PRG4 proteins and various isoforms are disclosed in, for instance, U.S. Pat. Nos. 5,326,558; 6,433,142; 7,030,223; 7,361,738 to Turner et al., and U.S. Pat. Nos. 6,743,774 and 6,960,562 to Jay et al. U.S. Publication No. 20070191268 to Flannery et al. also discloses recombinant PRG4 or lubricin molecules useful in the present invention.

Methods for isolation, purification, and recombinant expression of a PRG4 protein are well known in the art. In certain embodiments, the method starts with cloning and isolating mRNA and cDNA encoding PRG4 proteins or isoforms using standard molecular biology techniques, such as PCR or RT-PCR. The isolated cDNA encoding the PRG4 protein or isoform is then cloned into an expression vector, and further transformed and expressed in a host cell for producing recombinant PRG4 protein.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompasses the ligation of nucleic acids having various coding regions or domains or promoter sequences from different sources into an expression cassette or vector for expression of, e.g., inducible or constitutive expression of a fusion protein comprising an active domain of the PRG4 gene and a nucleic acid sequence amplified using a primer of the invention.

In certain embodiments, the PRG4 protein encoding nucleic acid may contain one or more mutations, deletions, or insertions. In such embodiments, the PRG4 protein encoding nucleic acid is at least 60% homology, preferably 75% homology, more preferably 85%, 90%, 95%, 96%, 97%, 98%, 99%, or more homology, to a wild type PRG4 protein encoding nucleic acid.

As used herein, the term "cDNAs" includes DNA that is complementary to mRNA molecules present in a cell or organism mRNA that can be converted into cDNA with an enzyme such as reverse transcriptase. In certain embodiments, the cDNA encoding PRG4 protein is isolated from PRG4 mRNA expressed in human corneal or conjunctival epithelial cells using an RT-PCR method well known in the art.

As used herein, the terms "polynucleotide," "nucleic acid/nucleotide," and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

As used herein, the term "polynucleotide sequence" is the alphabetical representation of a polynucleotide molecule. A polynucleotide is composed of a specific sequence of four nucleotide bases: adenine (A); cytosine (C); guanine (G); thymine (T); and uracil (U) in place of thymine when the polynucleotide is RNA, instead of DNA. This alphabetical representation can be inputted into databases in a computer and used for bioinformatics applications such as, for example, functional genomics and homology searching.

As used herein, the term "isolated polynucleotide/cDNA" includes polynucleotide molecules which are separated from other polynucleotide molecules which are present in the natural source of the polynucleotide. For example, with regard to genomic DNA, the term "isolated" includes polynucleotide molecules which are separated from the chromosome with which the genomic DNA is naturally associated. Preferably, an "isolated" polynucleotide is free of sequences which naturally flank the polynucleotide (i.e., sequences located at the 5' and 3' ends of the polynucleotide of interest) in the genomic DNA of the organism from which the polynucleotide is derived. For example, in various embodiments, the isolated polynucleotide molecule encoding the PRG4 protein used in the invention can contain less than about 5 kb, 4 kb, 3 kb, 2 kb, 1 kb, 0.5 kb or 0.1 kb of nucleotide sequences which naturally flank the polynucleotide molecule in genomic DNA of the cell from which the polynucleotide is derived. Moreover, an "isolated" polynucleotide molecule, such as a cDNA molecule, can be substantially free of other cellular material, or culture medium when produced by recombinant techniques, or substantially free of chemical precursors or other chemicals when chemically synthesized.

As used herein, a "gene" includes a polynucleotide containing at least one open reading frame that is capable of encoding a particular polypeptide or protein after being transcribed and translated. Any of the polynucleotide sequences described herein may also be used to identify larger fragments or full-length coding sequences of the gene with which they are associated. Methods of isolating larger fragment sequences are known to those of skill in the art. As used herein, a "native or naturally-occurring" polynucleotide molecule includes, for example, an RNA or DNA molecule having a nucleotide sequence that occurs in nature (e.g., encodes a natural protein).

As used herein, the term "polypeptide" or "protein" is interchangeable, and includes a compound of two or more subunit amino acids, amino acid analogs, or peptidomimetics. The subunits may be linked by peptide bonds. In another embodiment, the subunit may be linked by other bonds, e.g., ester, ether, etc. As used herein, the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

In certain embodiments, the PRG4 protein used herein refers to PRG4 proteins or various homologs or isoforms thereof, that are naturally or recombinantly expressed in humans or other host cells. As used herein, "express" or "expression" includes the process by which polynucleotides are transcribed into RNA and/or translated into polypeptides. If the polynucleotide is derived from genomic DNA, expression may include splicing of the RNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general. As used herein, the term "vector" includes a self-replicating nucleic acid molecule that transfers an inserted polynucleotide into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above function.

As used herein, a "host cell" is intended to include any individual cell or cell culture which can be, or has been, a recipient for vectors or for the incorporation of exogenous polynucleotides and/or polypeptides. It is also intended to include progeny of a single cell. The progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, insect cells, animal cells, and mammalian cells, including but not limited to murine, rat, simian or human cells. As used herein, a "host cell" also includes genetically modified cells. The term "genetically modified cells" includes cells containing and/or expressing a foreign or exogenous gene or polynucleotide sequence which in turn modifies the genotype or phenotype of the cell or its progeny. "Genetically modified" also includes a cell containing or expressing a gene or polynucleotide sequence which has been introduced into the cell. For example, in this embodiment, a genetically modified cell has had introduced a gene which gene is also endogenous to the cell. The term "genetically modified" also includes any addition, deletion, or disruption to a cell's endogenous nucleotides. As used herein, a "host cell" can be any cells that express a human PRG4 protein.

As used herein, "homologs" are defined herein as two nucleic acids or peptides that have similar, or substantially identical, nucleic acids or amino acid sequences, respectively. The term "homolog" further encompasses nucleic acid molecules that differ from one of the nucleotide sequences due to degeneracy of the genetic code and thus encodes the same amino acid sequences. In one of the preferred embodiments, homologs include allelic variants, orthologs, paralogs, agonists, and antagonists of nucleic acids encoding the PRG4 protein (e.g., SEQ ID NO:1).

As used herein, the term "orthologs" refers to two nucleic acids from different species, but that have evolved from a common ancestral gene by speciation. Normally, orthologs encode peptides having the same or similar functions. In particular, orthologs of the invention will generally exhibit at least 80-85%, more preferably 85-90% or 90-95%, and most preferably 95%, 96%, 97%, 98%, or even 99% identity, or 100% sequence identity, with all or part of the amino acid sequence of any known PRG4 proteins (e.g., SEQ ID NO:1), isoforms, or analogs thereof, and will exhibit a function similar to these peptides. As also used herein, the term "paralogs" refers to two nucleic acids that are related by duplication within a genome. Paralogs usually have different functions, but these functions may be related.

To determine the percent sequence identity of two amino acid sequences, the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence of any known PRG4 protein (e.g., SEQ ID NO:1).

In certain embodiments, an isolated nucleic acid homolog encoding the PRG4 protein comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence encoding amino acid sequences of such PRG4 protein (e.g., SEQ ID NO:1).

The determination of the percent sequence identity between two nucleic acid or peptide sequences is well known in the art. For instance, the Vector NTI 6.0 (PC) software package (InforMax, Bethesda, Md.) to determine the percent sequence identity between two nucleic acid or peptide sequences can be used. In this method, a gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

Furthermore, the PRG4 protein used herein includes PRG4 protein encoded by a polynucleotide that hybridizes to the polynucleotide encoding PRG4 protein under stringent conditions. As used herein, "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under different stringent conditions. The present invention includes polynucleotides capable of hybridizing under reduced stringency conditions, more preferably stringent conditions, and most preferably highly stringent conditions, to polynucleotides encoding PRG4 protein described herein. As used herein, the term "stringent conditions" refers to hybridization overnight at 60° C. in 10× Denhart's solution, 6×SSC, 0.5% SDS, and 100 mg/ml denatured salmon sperm DNA. Blots are washed sequentially at 62° C. for 30 minutes each time in 3×SSC/0.1% SDS, followed by 1×SSC/0.1% SDS, and finally 0.1× SSC/0.1% SDS. As also used herein, in certain embodiments, the phrase "stringent conditions" refers to hybridization in a 6×SSC solution at 65° C. In other embodiments, "highly stringent conditions" refer to hybridization overnight at 65° C. in 10×Denhart's solution, 6×SSC, 0.5% SDS and 100 mg/ml denatured salmon sperm DNA. Blots are washed sequentially at 65° C. for 30 minutes each time in 3×SSC/0.1% SDS, followed by 1×SSC/0.1% SDS, and finally 0.1× SSC/0.1% SDS. Methods for nucleic acid hybridizations are well known in the art. Accordingly, the PRG4 proteins encoded by nucleic acids used herein include nucleic acid having at least 60% homology, preferably 75% homology, more preferably 85%, more preferably 90%, most preferably 95%, 96%, 97%, 98%, 99% homology to a polynucleotide sequence that encodes a human PRG4 protein (e.g., SEQ ID NO:1) or a specific isoform or homolog thereof.

Moreover, the PRG4 proteins used herein can also be chimeric protein or fusion protein. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art. In certain embodiments of the present invention, the chimeric protein is a chimera of PRG4 protein with other PRG4 protein isoforms.

As used herein, an "isolated" or "purified" protein, polynucleotide or molecule means removed from the environment in which they naturally occur, or substantially free of cellular material, such as other contaminating proteins from the cell or tissue source from which the protein polynucleotide or molecule is derived, or substantially free from chemical precursors or other chemicals when chemically synthesized. The language "substantially free of cellular material" includes preparations separated from cellular components of the cells from which it is isolated or recombinantly produced or synthesized. In certain embodiments, the language "substantially free of cellular material" includes preparations of a PRG4 protein having less than about 30% (by dry weight) of other proteins (also referred to herein as a "contaminating protein"), more preferably less than about 20%, still more preferably less than about 10%, and most preferably less than about 5% of other proteins. When the protein or polynucleotide is recombinantly produced, it is also preferably substantially free of culture medium, i.e., culture medium represents less than about 20%, more preferably less than about 10%, and most preferably less than about 5% of the volume of the preparation of the protein of interest.

In certain embodiments, the present invention provides a pharmaceutical composition suitable for topical administration to an ocular surface of an individual in need a pharmaceutically effective concentration of a PRG4 inducing compound, an optional mucoadhesive agent, and, optionally, PRG4 suspended in an ophthalmically acceptable balanced salt solution, and in combination with one or more ophthalmically acceptable agents. The ophthalmically acceptable agents can be selected from the group consisting of an ophthalmically acceptable demulcent, excipient, astringent, vasoconstrictor, and emollient. As used herein, the term "effective concentration or amount" or "therapeutically effective concentration or amount" is intended to mean a nontoxic but sufficient concentration or amount of a PRG4 inducing compound, the PRG4, or the other therapeutic agents to provide the desired therapeutic effects. The concentration or amount that is effective will vary from subject to subject, depending on the age and general condition of the individual, the particular agents, and the like. Thus, it is not always possible to specify an exact effective concentration or amount. However, an appropriate effective concentration or amount in any individual case may be determined by one of ordinary skill in the art using routine experimentation. Furthermore, the exact effective concentration or amount of a PRG4 inducing compound, the PRG4 protein, or the other therapeutic agents incorporated into a composition or dosage form of the present invention is not critical, so long as the concentration is within a range sufficient to permit ready application of the solution or formulation so as to deliver an amount of the PRG4 inducing compound, the PRG4 protein, or the other active agents that is within a therapeutically effective range.

In certain embodiments, the pharmaceutically effective concentration of a PRG4 inducing compound is in a range of 0.0001-0.1% w/v, and the pharmaceutically effective concentration of PRG4 protein is in a range of 10-10,000 µg/mL, preferably 50-500 µg/mL, and more preferably 100-300 µg/mL. As used herein, the ophthalmically acceptable agents comprising the ophthalmically acceptable demulcents, excipients, astringents, vasoconstrictors, and emollients that are fully defined in the Code of Federal Regulations 21CFR349.

In certain embodiments, the pharmaceutical compositions described herein comprise a residence-time increasing agent that increases the residence time of the PRG4 inducing compound on the ocular surface. In some embodiments, the residence-time-increasing agent is present in an amount such that when the pharmaceutical composition is administered to the surface of an eye of an individual, a therapeutically effective amount of a PRG4 inducing compound described herein is retained upon the surface of the eye. In certain embodiments, the residence-time increasing agent is selected and/or is present in an amount such that the therapeutically effective amount of the PRG4 inducing compound is retained on the surface of the eye for any therapeutically effective period of time, at least 1 minute, at least 2 minutes, at least 5 minutes, at least 10 minutes, at least 15 minutes, at least 20 minutes, at least 30 minutes, at least 1 hour, or more. In certain embodiments, ophthalmically acceptable residence-time increasing agents or mucoadhesives may include, by way of non-limiting example, hydroxypropylmethylcellulose, carboxymethylcellulose, carbomer (acrylic acid polymer), poly(methylmethacrylate), polyacrylamide, polycarbophil, polyethylene oxide, acrylic acid/butyl acrylate copolymer, sodium alginate, dextran, or combinations thereof. The present invention encompasses any high molecular weight polymers that would increase the time that the PRG4 inducing compound remains on the surface of the eye.

As used herein, the term "topical administration" is used in its conventional sense to mean delivery of the composition comprising the PRG4 protein and one or more ophthalmically acceptable agents to the eye. In general, topical administration is achieved through a liquid formulation for eye drops or lavage and provides a local effect.

In certain embodiments, any pharmaceutical composition described herein comprise or the aforementioned ophthalmically acceptable agents are or can be combined with one or more of carboxymethylcellulose sodium (e.g., about 0.2 to about 2.5% w/v), hydroxyethyl cellulose (e.g., about 0.2 to about 2.5% w/v), hypromellose (e.g., about 0.2 to about 2.5% w/v), methylcellulose (e.g., about 0.2 to about 2.5% w/v), dextran 70 (e.g., about 0.1% w/v), gelatin (e.g., about 0.01% w/v), glycerin (e.g., about 0.2 to about 1% w/v), polyethylene glycol 300 (e.g., about 0.2 to about 1% w/v), polyethylene glycol 400 (e.g., about 0.2 to about 1% w/v), polysorbate 80 (e.g., about 0.2 to about 1% w/v), propylene glycol (e.g., about 0.2 to about 1% w/v), polyvinyl alcohol (e.g., about 0.1 to about 4% w/v), povidone (e.g., about 0.1 to about 2% w/v), zinc sulfate (e.g., about 0.25% w/v), anhydrous lanolin (e.g., about 1 to about 10% w/v), lanolin (e.g., about 1 to about 10% w/v), light mineral oil (e.g., ≤about 50% w/v), mineral oil (e.g., ≤about 50% w/v), paraffin (e.g., ≤about 5% w/v), petrolatum (e.g., ≤about 100% w/v), white ointment (e.g., ≤about 100% w/v), white petrolatum (e.g., ≤about 100% w/v), white wax (e.g., ≤about 5% w/v), yellow wax (e.g., ≤about 5% w/v), ephedrine hydrochloride (e.g., about 0.123% w/v), naphazoline hydrochloride (e.g., about 0.01 to about 0.03% w/v), phenylephrine hydrochloride (e.g., about 0.08 to about 0.2% w/v), and tetrahydrozoline hydrochloride (e.g., about 0.01 to about 0.05% w/v). In certain instances, percent amounts utilized herein are percent amounts by weight.

In further embodiments, any pharmaceutical composition of the present invention (e.g., a composition comprising a PRG4 inducing compound and PRG4) may further comprise a therapeutically effective concentration of hyaluronic acid or sodium hyaluronate in the range of 10-100,000 µg/mL, preferably 500-5,000 µg/mL. Furthermore, the pharmaceutical composition of the present invention may further comprise one or more surface active phospholipids in the range of 10-10,000 µg/mL, such surface active phospholipids include, but are not limited to, L-α-dipalmitoylphosphatidylcholine (DPPC), phosphatidylcholine (PC), phosphatidylethanolamine (PE) and sphingomyelin (Sp), or other neutral and polar lipids. In this embodiment, the combination of the more hydrophobic modulators with the amphiphilic boundary lubricant molecules allows the direct transport of therapeutically effective molecules to the ocular surface cells, where the boundary lubricant molecules tend to aggregate, and provides a pharmaceutically efficient carrier for therapeutic compounds to the corneal and conjunctival epithelium for efficient boundary lubrication. For example, solubilizing the hydrophobic androgens in DPPC, then complexing DPPC, HA and PRG4 in a pharmaceutically acceptable carrier, transports and concentrates the androgens at the ocular surface cells, where they may most efficiently upregulate boundary lubricant expression.

The pharmaceutical composition of the present invention may further comprise one or more pharmaceutically acceptable carriers or vehicles comprising any acceptable materials, and/or any one or more additives known in the art. As used herein, the term "carriers" or "vehicle" refer to carrier materials suitable for topical drug administration. Carriers and vehicles useful herein include any such materials known in the art, which are nontoxic and do not interact with other components of the composition in a deleterious manner. Various additives, known to those skilled in the art, may be included in the composition. For example, solvents, including relatively small amounts of alcohol, may be used to solubilize certain drug substances. Other optional additives include opacifiers, antioxidants, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. Permeation enhancers and/or irritation-mitigating additives may also be included in the pharmaceutical composition of the present invention.

In certain embodiments, the pharmaceutical composition of the present invention is prepared in a pharmaceutically acceptable carrier, such as a phosphate buffered saline or an osmotically balanced salt solution of tear electrolytes, including one or more of sodium chloride in about 44% to about 54% mole fraction, potassium chloride in about 8% to about 14% mole fraction, sodium bicarbonate in about 8% to about 18% mole fraction, potassium bicarbonate in about 0% to about 4% mole fraction, calcium chloride in about 0% to about 4% mole fraction, magnesium chloride in about 0% to about 4% mole fraction, trisodium citrate in about 0% to about 4% mole fraction, and hydrochloric acid in about 0% to about 20% mole fraction or sodium hydroxide in about 0% to about 20% mole fraction. In certain embodiments, the pharmaceutical carrier can be formulated to generate an aqueous electrolyte solution in about 150-200 mM range. Other suitable formulations, such as ointments, creams, gels, pastes, and the like, suitable for topical administration, are also contemplated in the present invention. In certain embodiments, electrolytes provide proper osmotic balance when combined with the PRG4 inducing compound and optional PRG4 to make a solution ophthalmically acceptable.

The present invention further provides a method for treating decreased or undesired ocular boundary lubrication, symptoms associated therewith, or a condition that is associated with or causes a deficiency in ocular lubrication, in an individual in need thereof, comprising topically administering to the ocular surface of the individual in need a any pharmaceutical composition described herein. In a specific embodiment, the composition comprises a therapeutically effective amount of a PRG4 inducing compound in combination with PRG4. In one embodiment, the method of the present invention comprises topically administering a pharmaceutical composition comprising the therapeutically effective amount of a PRG4 inducing compound in combination with PRG4 that is suspended in a phosphate buffered saline solution or an ophthalmically acceptable balanced salt solution comprising one or more tear electrolytes. In yet other embodiment, the method of the present invention comprising topically administering a pharmaceutical composition comprising a PRG4 inducing compound and PRG4 that is formulated in an ophthalmically acceptable formulation comprising one or more additional ophthalmically acceptable agent as discussed above.

As used herein, the term "treating or treatment" refers to reduction in severity and/or frequency of symptoms, elimination of symptoms and/or underlying cause, prevention of the occurrence of symptoms and/or their underlying cause, and improvement or remediation of damage. The term "treating or treatment" also encompasses both prevention of a disorder in a predisposed individual and treatment of the disorder in a clinically symptomatic individual.

In certain embodiments, the decreased ocular boundary lubrication is caused by increased evaporative tear loss or unstable tear film in the ocular boundary loop. Such decreased or undesired ocular boundary lubrication is associated with aqueous or evaporative dry eye disease, Sjögren's syndrome, keratoconjunctivitis sicca (KCS), androgen deficiency, meibomian gland disease, estrogen replacement therapy, contact lens wear, refractive surgery, allergy, reduced tear film breakup time, compromised tear film, ocular surface disorders, increased protease levels in the tear film and at the ocular surface, chronic inflammation, hyperosmolarity, and aging. As discussed above, the increased shear stress leads to tear film instability, evaporative tear loss, hyperosmolarity, changes in swelling pressure and a feedback elevation in shear stress. Increased shear stress also promotes inflammation, androgen deficiency and decreased expression of proteoglycans. Over time, increased shear stress and its sequelae leads to a loss of boundary lubrication at the ocular surface. Accordingly, the present invention provides a method for reducing shear stress by replenishing and enriching the expression of proteoglycans, such as PRG4 protein, at the ocular surface, using a PRG4 inducing compound as discussed above, so as to prevent or increase ocular boundary lubrication. A method of localizing PRG4 induction at the ocular surface is also provided in the present invention.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

Other features and advantages of the invention will be apparent from the following description of the preferred embodiments thereof and from the claims. These and many other variations and embodiments of the invention will be apparent to one of skill in the art upon a review of the appended description and examples.

EXAMPLES

Example 1

PRG4 mRNA Expression in Human Corneal and Conjunctival Epithelial Cells

Human corneal epithelial cells were isolated from the corneoscleral rims of male and female donors. Cells were processed either directly (n=8), or first cultured in phenol red-free keratinocyte serum free media (n=2). Bulbar conjunctivae (n=2), conjunctival impression cytology samples (n=9), immortalized human conjunctival epithelial cells after culture (n=1), NOD mouse lacrimal glands (n=5 adult mice/sex, 10 glands/sample), and BALB/c mouse meibomian glands (n=7 adult mice/sex, glands from 28 lids/sample) were obtained during surgical procedures. These samples were processed for the analysis of PRG4 mRNA by using primarily RT-PCR (n=18 human, all mouse) and Affymetrix GeneChips (n=4 human corneas). The PRG4 primers for PCR spanned over 1 kbp of intron sequences, in order to suppress amplification of contaminating chromosomal DNA (Table 1). Amplified samples were screened for the presence of PRG4 products by using agarose gel electrophoresis and an Agilent 2100 Bioanalyzer. To confirm the identity of amplicons, PCR products from cornea samples (n=2), conjunctival epithelial cells (n=1) and a human liver standard (n=1) were sequenced with a 3100 Genetic Analyzer at the Massachusetts Eye and Ear Infirmary DNA Sequencing Center for Vision Research (Boston, Mass.) and resulting data were analyzed with BLASTn searches of GenBank databases.

TABLE 1

Oligonucleotide primers designed for RT- PCR analysis of PRG4 mRNA

| Species | Orientation | Nucleotide sequence (5' - 3') | Exons | Amplicon Size (bp) |
|---|---|---|---|---|
| Human | Sense | GATGCAGGGTACCCCAAA (SEQ ID NO: 2) | 9-12 | 526 |
|  | Antisense | CAGACTTTGGATAAGGTCTGCC (SEQ ID NO: 3) |  |  |

It was demonstrated that PRG4 mRNA is present in all human corneal and conjunctival epithelial cell and impression cytology samples. The identity of PRG4 PCR products was confirmed by DNA sequence analysis (Table 2). The results show that PRG4 is transcribed in human corneal and conjunctival epithelial cells.

TABLE 2

Identification of amplicon sequences from human cornea, conjunctival and liver samples

| Sequencing Direction | Aligned Base Pairs To Human PRG4 | Total Base Pairs from Amplicon | BLASTn Search Identity |
|---|---|---|---|
| *Human Liver Standard* | | | |
| A Forward | 495 | 500 | Human PRG4 |
| A Reverse | 488 | 491 | Human PRG4 |
| B Forward | 496 | 499 | Human PRG4 |
| B Reverse | 498 | 500 | Human PRG4 |
| *Human Cornea (24 year old female)* | | | |
| A Forward | 497 | 499 | Human PRG4 |
| A Reverse | 490 | 492 | Human PRG4 |
| B Forward | 500 | 504 | Human PRG4 |
| B Reverse | 498 | 501 | Human PRG4 |
| *Human Cornea (51 year old female)* | | | |
| A Forward | 498 | 499 | Human PRG4 |
| A Reverse | 474 | 489 | Human PRG4 |
| B Forward | 496 | 498 | Human PRG4 |
| B Reverse | 490 | 491 | Human PRG4 |
| *Human Conjunctival Epithelial Cells* | | | |
| A Forward | 496 | 499 | Human PRG4 |
| A Reverse | 490 | 492 | Human PRG4 |
| B Forward | 495 | 499 | Human PRG4 |
| B Reverse | 474 | 491 | Human PRG4 |

Two different samples (A & B) of each preparation were sequenced in forward and reverse directions. The human cornea samples were epithelial cells from the corneoscleral rims of female donors. The gene accession number for human PRG4 is NM_005807.

Example 2

Regulation of PRG4 Expression In Vitro by Androgen

Figure 6:
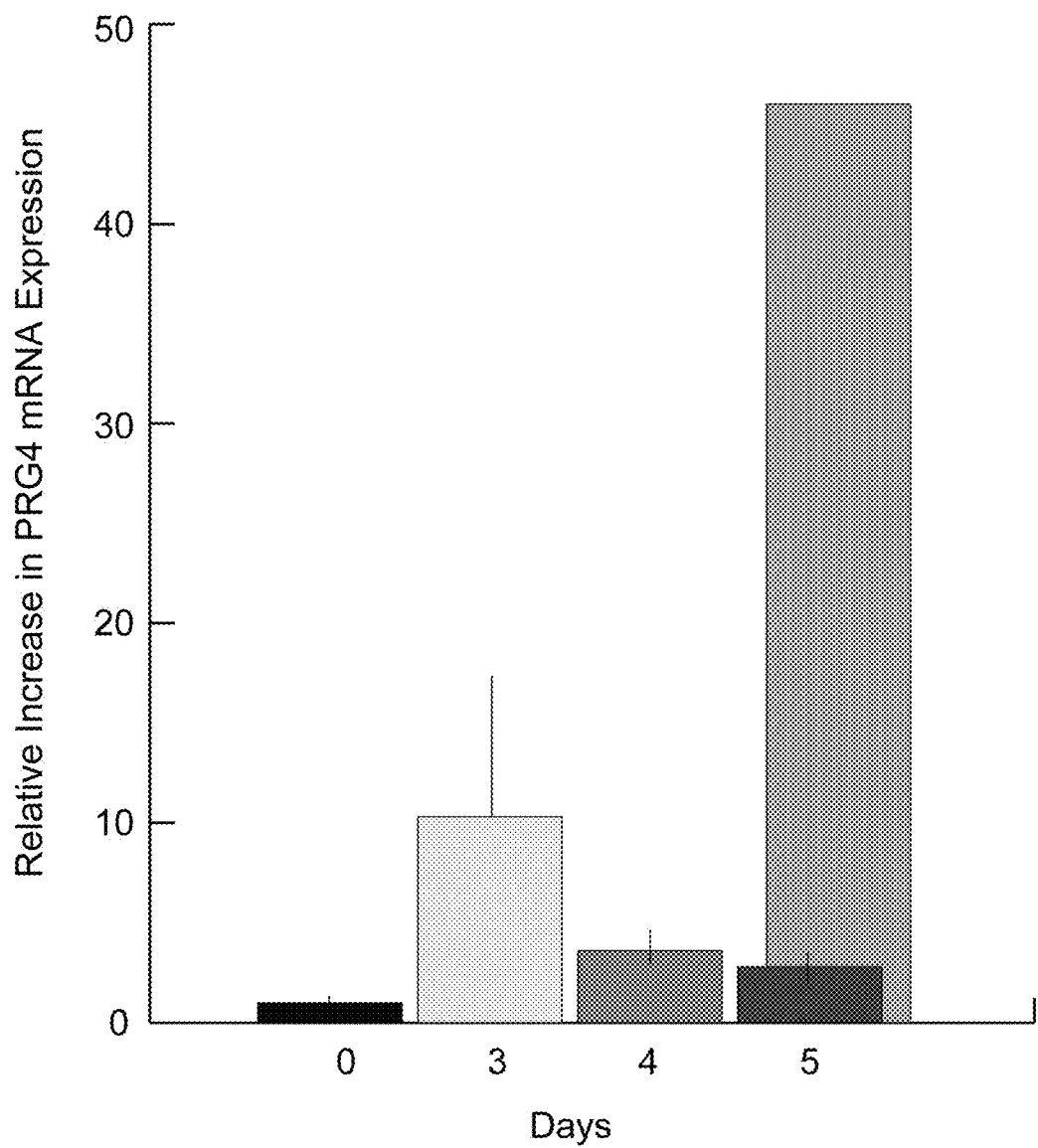
FIG. 6 illustrates time course of relative increase in PRG4 mRNA in primary corneal epithelial cells under the influence of 10 nM dihydrotestosterone. Cells were grown in keratinocyte serum free media until reaching about 80% confluence. Cells (n=3 wells/treatment/experiment) were then incubated with either vehicle or 10 nM dihydrotestosterone (DHT) for up to 5 days. At designated times cells were processed for total RNA isolation and analysis of PRG4 mRNA mRNA by RT-PCR. The results show that the DHT induces a marked increase in PRG4 mRNA levels in primary human corneal epithelial cells. This androgen effect, relative to the control levels at Day 0, became prominent after 3 (10.3-fold increase), 4 (3.6-fold increase) and 5 (2.8-fold increase) days of hormone exposure. This DHT influence on PRG4 mRNA expression in primary human corneal epithelial cells was confirmed in another experiment. Treatment of cells for 5 days with DHT caused a 46-fold increase in PRG4 mRNA content, relative to that of vehicle-treated controls.

Androgen treatment upregulates PRG4 mRNA expression in primary human corneal epithelial cells. Methods. Cells were grown in keratinocyte serum free media until reaching about 80% confluence. Cells (n=3 wells/treatment/experiment) were then incubated with either vehicle or 10 nM dihydrotestosterone (DHT) for up to 5 days. At designated times cells were processed for total RNA isolation and analysis of PRG4 mRNA mRNA by RT-PCR. Results. The results show that the DHT induces a marked increase in PRG4 mRNA levels in primary human corneal epithelial cells (FIG. 6). This androgen effect, relative to the control levels at Day 0, became prominent after 3 (10.3-fold increase), 4 (3.6-fold increase) and 5 (2.8-fold increase) days of hormone exposure. This DHT influence on PRG4 mRNA expression in primary human corneal epithelial cells was confirmed in another experiment. Treatment of cells for 5 days with DHT caused a 46-fold increase in PRG4 mRNA content, relative to that of vehicle-treated controls.

Combined 17β-estradiol and progesterone treatment downregulates PRG4 mRNA expression in mouse lacrimal tissue. Age-matched and young adult BALB/c mice, that were ovariectomized when 8 weeks old, were purchased from Taconic Laboratories (Germantown, N.Y.). Animals were maintained in constant temperature rooms with fixed light/dark period of 12 hours duration. Ten days after surgery, pellets containing vehicle (cholesterol, methylcellulose, lactose), or 17β-estradiol (0.5 mg) plus progesterone (10 mg), were implanted subcutaneously in the ovariectomized mice. The pellets were obtained from Innovative Research of America (Sarasota, Fla.) and were designed for the constant release of placebo or physiological amounts of sex steroid (i.e. as in pregnancy) for 3 weeks. After 14 days of treatment, mice (n=7 mice/condition/experiment) were sacrificed by $CO_2$ inhalation and exorbital lacrimal glands were removed, pooled according to group (n=14 glands/sample) and processed for molecular biological procedures.

Total RNA was extracted from tissues by using TRIzol reagent (Invitrogen Corp., Carlsbad, Calif.). When indicated, samples were also exposed to RNase-free DNase (Invitrogen), examined spectrophotometrically at 260 nm to determine concentration and evaluated on 6.7% formaldehyde/1.3% agarose (Gibco/BRL, Grand Island, N.Y.) gels to verify RNA integrity. The RNA samples were further purified with RNAqueous spin columns (Ambion, Austin, Tx), and the integrity of these preparations was assessed with a RNA 6000 Nano LabChip with an Agilent 2100 Bioanalyzer (Agilent Technologies, Palo Alto, Calif.). The RNA samples were then processed for CodeLink Bioarray hybridization. In brief, cDNA was synthesized from RNA (2 μg) with a CodeLink Expression Assay Reagent Kit (Amersham, Piscataway, N.J.) and purified with a QIAquick purification kit (Qiagen, Valencia, Calif.). After sample drying, cRNA was made with a CodeLink Expression Assay Reagent Kit (Amersham), recovered with an RNeasy kit (Qiagen) and quantified with an UV spectrophotometer. Fragmented, biotin-labeled cRNA was then incubated and agitated (300 rpm shaker) on a CodeLink Bioarray at 37° C. for 18 hours. The Bioarray was washed, exposed to streptavidin-Alexa 647, and scanned by using ScanArray Express software and a ScanArray Express HT scanner (Packard BioScience, Meriden, Conn.) with the laser set at 635 nm, laser power at 100%, and photomultiplier tube voltage at 60%. Scanned image files were evaluated by utilizing CodeLink image and data analysis software (Amersham), which produced both raw and normalized hybridization signal intensities for each array spot. The spot intensities (40,000) on the microarray image were standardized to a median of 1. Normalized data, with signal intensities exceeding 0.75, were analyzed with GeneSifter.Net software (VizX Labs LLC, Seattle, Wash., vizxlabs.com). Statistical analysis of individual gene expression data was performed with Student's t-test (two-tailed, unpaired).

The data show that combined estradiol and progesterone treatment, as compared to that of placebo, causes a significant (p=0.020), 1.6-fold decrease in PRG4 gene expression in the mouse lacrimal gland.

Example 3

Treatment of Deficient Ocular Boundary Lubrication In Vivo with Androgen and PRG4

A patient complaining of ocular surface irritation is examined for ocular lubrication or conditions associated with a deficiency in ocular lubrication by measuring symptoms greater than 2 positive responses on the McMonnies questionnaire, greater than a score of 5 on the Ocular Surface Disease Index (OSDI), or through evidence of some symptoms on the Visual Analog Scale, in combination with objective signs including one or more of a reduced tear film breakup time (less than ≈10 seconds), inferior lateral tear meniscus osmolarity greater than 308 mOsms/L, low Schirmer strip value (less than ≈10 mm), sodium fluorescein corneal or conjunctival staining (scores >0 with multiple macropunctates), significant debris resulting from impression cytology, meibomian gland dysfunction however determined, a decrease in the rate of post-blink displacement of a contact lens, a change in the spatiotemporal transfer function of a contact lens following application of a series of pressure impulses, a decrease in the rate of post-blink interferometric tear film relaxation, an increase in the concentration of proinflammatory cytokines, a reduced concentration of lactoferrin or lysozyme, or an increase in the rate of post-blink point spread function decoherence.

The patient administers 1 to 2 drops on the surface of each eye a solution containing 4,5a-dihydrotestosterone and 200 μg/mL PGR4 protein suspended in an ophthalmically acceptable balanced salt solution. The patient is instructed to close their eyes for 10 seconds.

Follow-up visits may track a reduction in inferior lateral tear osmolarity, increased tear film breakup time, or the other aforementioned signs. In particular if the tear film osmolarity is reduced from an abnormal value (perhaps 330 mOsms/L) to a more normal value (perhaps 304 mOsms/L), the therapeutic modulation and replenishment of the ocular surface lubrication would be deemed successful.

REFERENCES

1. G. D. Jay, Curr Opin Orthop 15, 355 (2004).
2. Schumacher B L, Hughes C E, Kuettner K E, Caterson B, Aydelotte M B. Immunodetection and partial cDNA sequence of the proteoglycan, superficial zone protein, synthesized by cells lining synovial joints. J Orthop Res. 1999 January; 17(1):110-20.
3. S. G. Rees et al., Matrix Biology 21, 593 (2002).
4. Schumacher B L, Schmidt T A, Voegtline M S, Chen A C, Sah R L. Proteoglycan 4 (PRG4) synthesis and immunolocalization in bovine meniscus. J Orthop Res. 2005 May; 23(3):562-8.
5. J. Marcelino et al., Nat Genet 23, 319 (1999).
6. D. K. Rhee et al., J Clin Invest 115, 622 (2005).
7. Cutolo M, Capellino S, Sulli A, Serioli B, Secchi M E, Villaggio B, Straub R H. Estrogens and autoimmune diseases. Ann N Y Acad Sci 2006; 1089:538-547.
8. Cutolo M, Sulli A, Capellino S, Villaggio B, Montagna P, Pizzorni C, Paolino S, Seriolo B, Felli L, Straub R H. Anti-TNF and sex hormones. Ann N Y Acad Sci 2006; 1069:391-400.
9. Rontzsch A, Thoss K, Petrow P K, Henzgen S, Brauer R. Amelioration of murine antigen-induced arthritis by dehydroepiandrosterone (DHEA). Inflamm Res 2004; 53:189-198.
10. Schwarz I M, Hills B A, Br. J. Rheum. 1998; 37:21-26.
11. Jay G D, Hong B S. Connect Tissue Res, 1992; 28(1-2): 89-98.
12. Jones M B. et. al. Mathematical Medicine and Biology 2005; 22, 265.
13. E. Meyer, R. M. Overney, K. Dransfeld, T. Gyalog, Nanoscience: Friction and Rheology on the Nanometer Scale (World Scientific Publishing Co. Pte. Ltd, River Edge, N.J., 2002), pp. 373.
14. D. Dowson, Proc Inst Mech Eng [H] 215, 335 (2001).
15. G. A. Ateshian, V. C. Mow, in Basic Orthopaedic Biomechanics and Mechano-Biology V. C. Mow, R. Huiskes, Eds. (Lippincott Williams & Wilkins, Philadelphia, 2005) pp. 447-494.
16. F. Guilak, Arthritis Rheum 52, 1632 (June, 2005).
17. K. C. Morell, W. A. Hodge, D. E. Krebs, R. W. Mann, Proc Natl Acad Sci USA 102, 14819 (Oct. 11, 2005).
18. S. A. V. Swanson, in Adult Articular Cartilage M. A. R. Freeman, Ed. (Pitman Medical, Tunbridge Wells, England, 1979) pp. 415-460.
19. K. C. Morrell, W. A. Hodge, D. E. Krebs, R. W. Mann, Proc Natl Acad Sci USA 102, 14819 (Oct. 11, 2005).
20. C. W. McCutchen, Fed Proceedings 25, 1061 (1966).
21. T. Murakami, Y. Sawae, M. Ihara, JSME Int J Series C-Mechanical Systems Machine Elements & Manufacturing 46, 594 (2003).
22. G. Meachim, Ann Rheum Dis 31, 457 (1972).
23. Schmidt M, Naumann H, Weidler C, Schellenberg M, Anders S, Straub R H. Inflammation and sex hormone metabolism. Ann N Y Acad Sci 2006; 1069:236-246.

What is claimed is:

1. A pharmaceutical composition effective to reduce osmolarity at the tear film comprising
   (i) PRG4 or a lubricating fragment thereof comprising glycosylated repeats of the sequence KEPAPTT, and
   (ii) an androgen, an androgen analogue, or a selective androgen receptor modulator selected from the group consisting of 17α-methyl-17β-hydroxy-2-oxa-5α-androstan-3-one or a derivative, testosterone or a derivative, 4,5α-dihydrotestosterone or a derivative, a 17β-hydroxy-5α-androstane containing a ring A unsaturation or a derivative, 19-nortestosterone or a derivative, a nitrogen-substituted androgen, an arylproprionamide compound, a bicyclic hydantoin analogue, a tetrahydroquinoline analogue, a quinoline analogue, S-3-(4-acetylamino-phenoxy)-2-hydroxy-2-methyl-N-(4-nitro-3-trifluoromethyl-phenyl)-propionamide [S-4]; and S-3-(4-flurophenoxy)-2-hydroxy-2-methyl-N-(4-nitro-3-trifluoromethyl-phenyl)-propionamide[S-1]).

2. The pharmaceutical composition of claim 1, effective to treat dry eye disease or a symptom caused by or associated with Sjogren's syndrome, keratoconjunctivitis sicca, androgen deficiency, meibomian gland disease, estrogen replacement therapy, contact lens wear, refractive surgery, allergy, reduced tear film breakup time, compromised tear film, ocular surface disorders, increased protease levels in the tear film and at the ocular surface, chronic inflammation, hyperosmolarity, aging, and combinations thereof.

3. The pharmaceutical composition of claim 1, effective to reduce tear osmolarity so as to relieve dysfunction of tear film.

4. The pharmaceutical composition of claim 1, wherein the composition comprises 10-10,000 μg/mL of PRG4.

5. The pharmaceutical composition of claim 1, wherein the composition comprises 50-500 μg/mL of PRG4.

6. The pharmaceutical composition of claim 1, wherein the composition comprises 100-300 μg/mL of PRG4.

7. The pharmaceutical composition of claim 1, wherein the composition comprises 200 μg/mL of PRG4.

8. The pharmaceutical composition of claim 1, wherein PRG4 or the lubricating fragment thereof has an average molar mass of between 50 kDa and 400 kDa.

9. The pharmaceutical composition of claim 1, wherein PRG4 or the lubricating fragment thereof is a recombinant or isolated polypeptide.

10. The pharmaceutical composition of claim 9, wherein PRG4 or the lubricating fragment thereof comprises an amino acid sequence that is at least 75% identical to SEQ ID NO:1.

11. The pharmaceutical composition of claim 1, wherein the composition comprises 0.0001-0.1% w/v of the androgen, the androgen analogue, or the selective androgen receptor modulator.

12. The pharmaceutical composition of claim 1, wherein the composition further comprises sodium hyaluronate or hyaluronic acid.

13. The pharmaceutical composition of claim 12, wherein the composition comprises 10-100,000 μg/mL of sodium hyaluronate or hyaluronic acid.

14. The pharmaceutical composition of claim 12, wherein the composition comprises 500-5,000 μg/mL of sodium hyaluronate or hyaluronic acid.

15. The pharmaceutical composition of claim 1, wherein the composition further comprises at least one surface active phospholipid selected from the group consisting of L-α-dipalmitoylphosphatidylcholine, phosphatidylcholine, phosphatidylethanolamine, and sphingomyelin.

16. The pharmaceutical composition of claim 15, wherein the composition comprises 10-10,000 μg/mL of the surface active phospholipid.

17. The pharmaceutical composition of claim 1, wherein the composition further comprises a phosphate buffered saline solution, or an ophthalmically acceptable balanced salt solution comprising a therapeutically effective concentration of one or more electrolytes selected from the group consisting of sodium phosphate, sodium chloride, potassium chloride, sodium bicarbonate, potassium bicarbonate, calcium chloride, magnesium chloride, trisodium citrate, hydrochloric acid, and sodium bicarbonate.

18. The pharmaceutical composition of claim 1, wherein the composition further comprises an ophthalmic demulcent, an excipient, an astringent, a vasoconstrictor, or an emollient.

19. The pharmaceutical composition of claim 1, wherein the composition further comprises a residence-time increasing agent.

20. The pharmaceutical composition of claim 19, wherein the residence-time increasing agent is selected from the group consisting of hydroxypropylmethylcellulose, carboxymethylcellulose, carbomer, acrylic acid polymer, polymethylmethacrylate, polyacrylamide, polycarbophil, polyethylene oxide, acrylic acid/butyl acrylate copolymer, sodium alginate, dextran, and combinations thereof.

* * * * *

UNITED STATES PATENT AND TRADEMARK OFFICE
CERTIFICATE OF CORRECTION

| | |
|---|---|
| PATENT NO. | : 9,421,241 B2 |
| APPLICATION NO. | : 14/831317 |
| DATED | : August 23, 2016 |
| INVENTOR(S) | : Benjamin Sullivan, Tannin A. Schmidt and David A. Sullivan |

It is certified that error appears in the above-identified patent and that said Letters Patent is hereby corrected as shown below:

In the Specification

Column 1, before Line 15, please insert the following paragraph:
--GOVERNMENT FUNDING
This invention was made with government support under EY005612 awarded by the National Institutes of Health. The government has certain rights in the invention.--

Signed and Sealed this
Ninth Day of May, 2023

Katherine Kelly Vidal
*Director of the United States Patent and Trademark Office*